United States Patent
Campbell

(10) Patent No.: US 7,771,484 B2
(45) Date of Patent: Aug. 10, 2010

(54) MODULAR TIBIAL IMPLANT

(75) Inventor: Michael N. Campbell, Elmwood, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1200 days.

(21) Appl. No.: 11/364,700

(22) Filed: Feb. 28, 2006

(65) Prior Publication Data

US 2007/0203582 A1  Aug. 30, 2007

(51) Int. Cl.
*A61F 2/38* (2006.01)

(52) U.S. Cl. .................. 623/20.34; 623/20.32

(58) Field of Classification Search .... 623/20.32–20.34
See application file for complete search history.

(56) References Cited

U.S. PATENT DOCUMENTS

| | | | |
|---|---|---|---|
| 4,834,081 A | | 5/1989 | Van Zile |
| 4,923,472 A | | 5/1990 | Ugolini |
| 4,936,847 A | | 6/1990 | Manginelli |
| 4,936,853 A | | 6/1990 | Fabian et al. |
| 4,938,769 A | * | 7/1990 | Shaw ................. 623/20.15 |
| 4,944,756 A | | 7/1990 | Kenna |
| 4,944,757 A | * | 7/1990 | Martinez et al. ......... 623/20.15 |
| 5,074,880 A | | 12/1991 | Mansat et al. |
| 5,152,796 A | | 10/1992 | Slamin |
| 5,152,797 A | | 10/1992 | Luckman et al. |
| 5,326,359 A | | 7/1994 | Oudard |
| 5,405,396 A | * | 4/1995 | Heldreth et al. ......... 623/20.32 |
| 5,413,605 A | | 5/1995 | Ashby et al. |
| 5,556,433 A | | 9/1996 | Gabriel et al. |
| 5,782,925 A | * | 7/1998 | Collazo et al. ........... 623/20.28 |
| 5,879,394 A | * | 3/1999 | Ashby et al. ............. 623/20.33 |
| 5,928,286 A | | 7/1999 | Ashby et al. |
| 6,258,127 B1 | | 7/2001 | Schmotzer |

(Continued)

FOREIGN PATENT DOCUMENTS

EP    1413264 A2    4/2004

(Continued)

OTHER PUBLICATIONS

U.S. Appl. No. 11/133,014, D'Allessio.

(Continued)

*Primary Examiner*—William H. Matthews
*Assistant Examiner*—Jacqueline Woznicki
(74) *Attorney, Agent, or Firm*—Lerner, David, Littenberg, Krumholz & Mentlik, LLP

(57) ABSTRACT

A modular tibial implant includes a tibial baseplate having a top surface, a bottom surface, and first and second openings extending between the top and bottom surfaces, and a bone engaging element having a distal end, a proximal end, and a longitudinal axis extending between the distal and proximal ends, the proximal end of the bone engaging element having a threaded opening alignable with the first opening of the tibial baseplate and a post insertible into the second opening of the tibial baseplate. The implant include a threaded fastener insertible into the aligned first opening and threaded opening, wherein the threaded fastener is rotatable for securing the proximal end of the bone engaging element to the bottom surface of the tibial baseplate, and a cam element insertible into the second opening of the tibial baseplate for engaging the post. The cam element is rotatable for moving the baseplate relative to the bone engaging element along an axis that traverses the longitudinal axis of the bone engaging element.

11 Claims, 25 Drawing Sheets

U.S. PATENT DOCUMENTS

| | | | |
|---|---|---|---|
| 6,299,645 B1 | 10/2001 | Ogden | |
| 6,506,216 B1 | 1/2003 | McCue et al. | |
| 6,602,255 B1 * | 8/2003 | Campbell et al. | 606/290 |
| 6,620,198 B2 | 9/2003 | Burstein et al. | |
| 6,719,800 B2 | 4/2004 | Meyers et al. | |
| 6,749,638 B1 | 6/2004 | Saladino | |
| 6,866,683 B2 | 3/2005 | Gerbec et al. | |
| 6,887,267 B2 | 5/2005 | Dworschak et al. | |
| 2003/0093082 A1 * | 5/2003 | Campbell et al. | 606/104 |
| 2003/0158606 A1 | 8/2003 | Coon et al. | |
| 2003/0171757 A1 | 9/2003 | Coon et al. | |
| 2003/0204263 A1 | 10/2003 | Justin et al. | |
| 2004/0073315 A1 | 4/2004 | Justin et al. | |
| 2004/0102852 A1 | 5/2004 | Johnson et al. | |
| 2004/0117023 A1 | 6/2004 | Gerbec et al. | |
| 2004/0117024 A1 | 6/2004 | Gerbec et al. | |
| 2004/0225368 A1 | 11/2004 | Plumet et al. | |
| 2005/0102031 A1 | 5/2005 | Leonard | |
| 2005/0149027 A1 * | 7/2005 | Campbell et al. | 606/70 |
| 2005/0209702 A1 | 9/2005 | Todd et al. | |
| 2006/0195195 A1 * | 8/2006 | Burstein et al. | 623/20.33 |
| 2006/0195196 A1 | 8/2006 | Pendleton et al. | |
| 2009/0204115 A1 * | 8/2009 | Dees et al. | 606/62 |

OTHER PUBLICATIONS

U.S. Appl. No. 11/177,087, Collazo.
Product Information, Stryker Howmedica, Take a Step Closer to Natural Motion, InteraxISA . . . a step closer to natural motion.

* cited by examiner

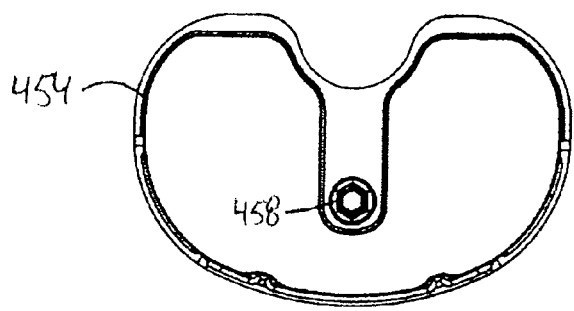
FIG. 42A
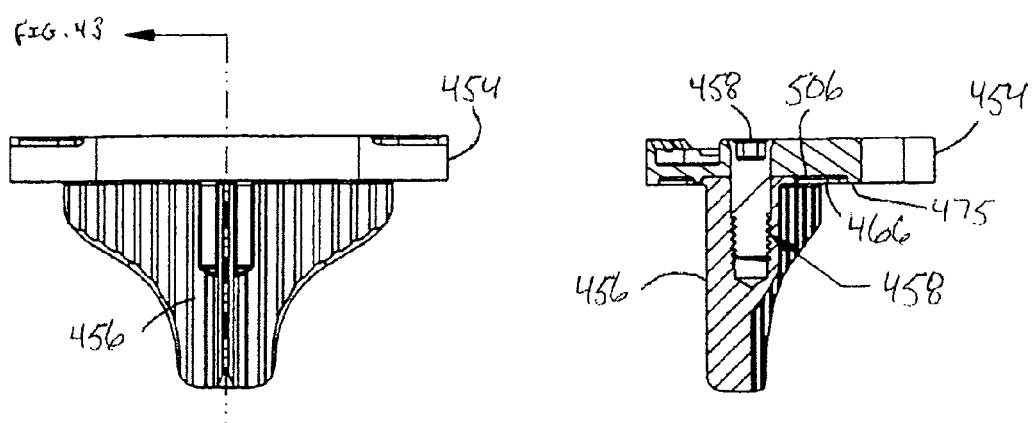
FIG. 42B
FIG. 43
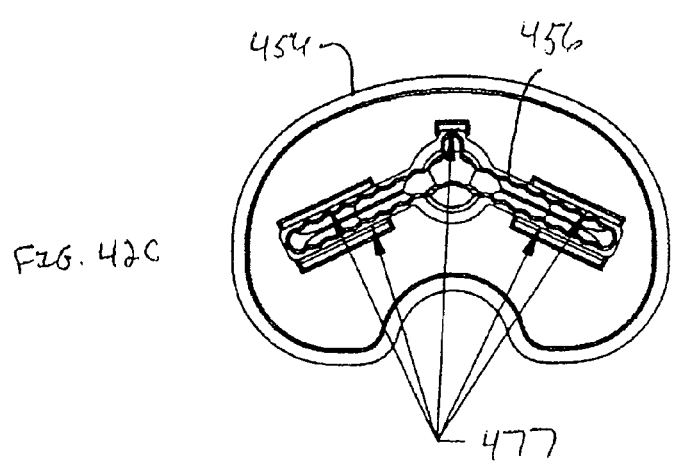
FIG. 42C

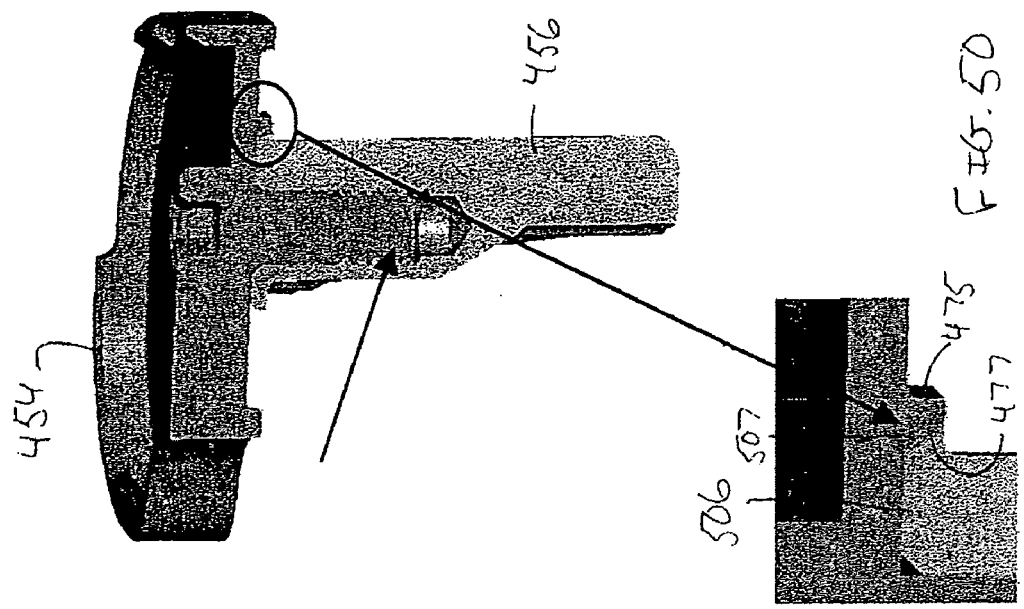
FIG. 49
FIG. 50
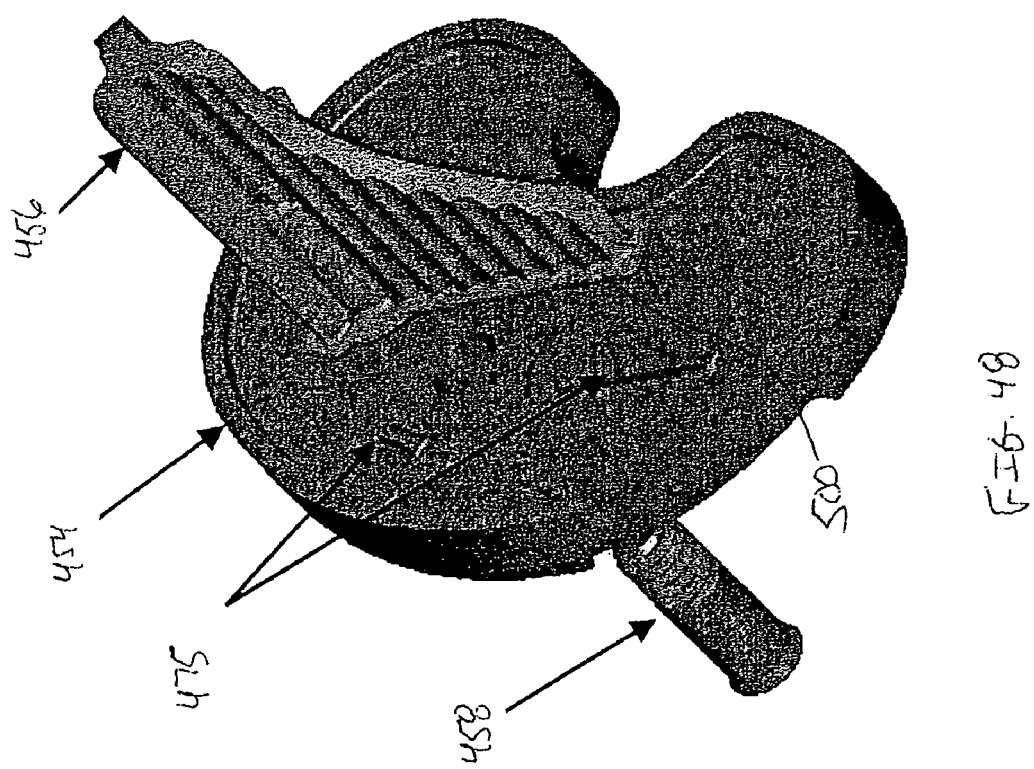
FIG. 48

US 7,771,484 B2

MODULAR TIBIAL IMPLANT

BACKGROUND OF THE INVENTION

The present invention relates to a modular tibial implant for use in total knee arthroplasty. More particularly, it relates to a modular tibial implant for use in Minimally Invasive Surgery (MIS) wherein all of the components can be installed through an incision on either the medial side or lateral side or on an anterior-lateral or anterior-medial location on the knee.

In the past, resurfacing of a knee joint was performed with the implantation of prosthetic femoral and tibial components through an incision extending proximally to distally along the anterior surface of the knee adjacent the lateral or medial sides of the patella. This required a comparatively long incision to be made in order to install the prosthetic femoral and tibial components. Recently, there has been progress towards shortening the incision and moving the incision either medially or laterally from the prior art anterior incision. While direct medial or lateral approaches are possible, it is preferred to have an anterior-medial or anterior-lateral approach.

U.S. Patent Publication No. 2003/0171757 relates to such a minimally invasive total knee arthroplasty method and instrumentation used therefor. In addition, co-pending, commonly assigned U.S. application Ser. No. 10/768,520, the disclosure of which is hereby incorporated by reference herein, teaches instrumentation used during minimally invasive procedures.

The size of incisions, while of secondary importance to not everting or subluxing the patella, has been reduced and may be in the range of 7-9 cm. Consequently it has been found necessary to utilize femoral and tibial prosthetic implants, which are adapted to be inserted through this reduced incision. One way of producing such an implant is to make the parts of the implant modular so that they may be inserted into a prepared knee in series. For example, with respect to the tibia, a typical tibial implant includes a stem or a keel, a baseplate and a modular bearing insert typically made of a polymeric material such as ultra-high molecular weight polyethylene.

Modular prosthetic knee components are known and are shown in U.S. Pat. Nos. 5,152,796, 5,326,359, 6,258,127, 6,506,216, and 5,413,605. These patents relate to methods of attaching modular stems or keels to a femoral or tibial component.

In spite of the above advances, there remains a need for improved modular tibial implants that are safe, reliable, cost effective and easy to implant during a surgical procedure.

SUMMARY OF THE INVENTION

In certain preferred embodiments of the present invention, a modular tibial implant includes a tibial baseplate having a top surface and a bottom surface, and a bone engaging element having a distal end, a proximal end, and a longitudinal axis extending between the distal and proximal ends. The implant desirably includes a fastener engageable with the tibial baseplate and the bone engaging element for securing the tibial baseplate and the bone engaging element together, and a cam element separate from the fastener and being engageable with the tibial baseplate and the bone engaging element for moving the baseplate relative to the bone engaging element along an axis that traverses the longitudinal axis of the bone engaging element.

In other preferred embodiments of the present invention, a modular tibial implant includes a tibial baseplate having a top surface, a bottom surface, and first and second openings extending between the top and bottom surfaces. The implant desirably includes a bone engaging element, such as a keel or stem, having a distal end, a proximal end, and a longitudinal axis extending between the distal and proximal ends, the proximal end of the bone engaging element having a threaded opening alignable with the first opening of the tibial baseplate and a post insertible into the second opening of the tibial baseplate. The implant may include a threaded fastener insertible into the aligned first opening and the threaded opening, whereby the threaded fastener is rotatable for securing the bone engaging element and the tibial baseplate together. The implant also desirably includes a cam element insertible into the second opening of the tibial baseplate for engaging the post, whereby the cam element is adjustable for moving the baseplate relative to the bone engaging element. The movement is preferably along an axis that traverses the longitudinal axis of the bone engaging element.

In certain preferred embodiments, the cam element is rotatable. The cam element preferably has an asymmetrical surface that engages the post located at the proximal end of the bone engaging element. The post may have a cross-section that is elongated along an axis. In certain preferred embodiments, the post may have an oval or oblong shaped cross-section.

In preferred embodiments, the tibial baseplate has a periphery and a pin opening extending between the periphery and the second opening of the tibial baseplate. The pin opening is desirably in communication with the second opening of the tibial baseplate. After the cam element is inserted into the second opening of the tibial baseplate, a pin may be inserted into the pin opening for engaging the cam element. The cam element may have a groove formed in an outer surface thereof and the pin desirably engages the groove for limiting movement and/or rotation of the cam element. The cam element desirably has an opening having an asymmetrical surface that engages an outer surface of the post at the proximal end of the bone engaging element for moving the tibial baseplate relative to the bone engaging element when the cam element is rotated.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

In other preferred embodiments of the present invention, a modular tibial implant includes a tibial baseplate having a top surface, a bottom surface, a peripheral region and a rim extending around the peripheral region. The implant preferably includes a bone engaging element having a distal end for engaging bone and a proximal end adapted for coupling with the bottom surface of the tibial baseplate. The tibial baseplate preferably includes a barrier wall projecting from the bottom surface of the tibial baseplate, whereby the barrier wall extends below the rim of the tibial baseplate. After assembly of the baseplate and the bone engaging element, the proximal end of the bone engaging element contacts the bottom surface of the tibial baseplate and the barrier wall surrounds the proximal end of the bone engaging element.

Although the present invention is not limited by any particular theory of operation, it is believed that the barrier wall prevents bone cement or adhesive from coming in contact with the joint formed between the proximal end of the bone engaging element and the bottom surface of the tibial baseplate, which in turn reduces the likelihood that the bone cement or adhesive will migrate to the top surface of the tibial baseplate. As is well known to those skilled in the art, the presence of bone cement or adhesive at the top surface of a tibial baseplate may result in damage to the bearing insert placed atop the top surface of the baseplate. Thus, the barrier wall performs numerous functions including dramatically reducing the likelihood that bone cement or adhesive will migrate to the top surface of the tibial baseplate where it will contact the bearing insert.

In certain preferred embodiments, the proximal end of the bone engaging element has a first contour and the barrier wall has a second contour that generally tracks the first contour at the proximal end of the bone engaging element.

In another preferred embodiment of the present invention, a modular tibial implant includes a tibial baseplate having a top surface, a bottom surface and alignment elements projecting from the bottom surface thereof. The alignment elements desirably have sloping edges. The implant also preferably includes a bone engaging element having a distal end for engaging bone and a proximal end adapted for coupling with the bottom surface of the tibial baseplate. The proximal end of the bone engaging element desirably has a bearing surface with sloping edges that mirror the sloping edges of the alignment elements. The sloping edges of the bearing surface are engageable with the sloping edges of the alignment elements for coupling the proximal end of the bone engaging element and the bottom surface of the tibial baseplate.

The tibial baseplate desirably has a rim extending around a periphery thereof and a barrier wall projecting from the bottom surface of the tibial baseplate. The barrier wall preferably extends below the rim of the tibial baseplate. After assembly, the barrier wall desirably surrounds both the alignment elements and the bearing surface of the bone engaging element that is coupled with the tibial baseplate.

The implant may include a threaded fastener in contact with the tibial baseplate and the bone engaging element for securing the tibial baseplate and the bone engaging element together. In other preferred embodiments, the implant may include a cam element in contact with the tibial baseplate and the bone engaging element. The cam element is adjustable for moving the tibial baseplate relative to the bone engaging element. Adjusting the cam element moves the tibial baseplate relative to the bone engaging element along an axis that is substantially parallel to the top surface of the tibial baseplate.

In other preferred embodiments of the present invention, a modular tibial implant includes a tibial baseplate having a top surface, a bottom surface, and an opening extending from the top surface to the bottom surface, the opening being tapered and having an oblong-oval shape with opposing sides that are flat and opposing ends that are curved. The implant also desirably includes a bone engaging element having a distal end for engaging bone, and a proximal end adapted for coupling with the tibial baseplate, the proximal end including a projection being tapered and having an oblong-oval shape with opposing sides that are flat and opposing ends that are curved. The tapered post is insertible into the tapered opening for forming a taper lock therebetween so as to secure the tibial baseplate and the bone engaging element together. In other preferred embodiments, the tapered opening and the tapered projection have an oval shape. In still other preferred embodiments, the oblong-oval or oval shaped tapered projection may be located on the tibial baseplate and the oblong-oval or oval shaped tapered opening may be located at the proximal end of the bone engaging element.

In still another preferred embodiment of the present invention, a modular tibial implant includes a tibial baseplate having a top surface, a bottom surface, and an elongated projection extending from the bottom surface. The elongated projection is preferably tapered and has an oblong-oval shape with opposing sides that are flat and opposing ends that are curved. The implant may include a bone engaging element having a distal end for engaging bone and a proximal end adapted for coupling with the tibial baseplate, the proximal end including an opening being tapered and having an oblong-oval shape with opposing sides that are flat and opposing ends that are curved. The tapered post is insertible into the tapered opening for forming a taper lock therebetween so as to secure the tibial baseplate and the bone engaging element together. The implant may include a fastener, such as a threaded fastener, for holding the tibial baseplate and the bone engaging element together. The fastener may extend through the tapered projection and the tapered opening. In other preferred embodiments, the tapered projection and the tapered opening may have an oval shape.

In another preferred embodiment of the present invention, a tibial implant may include any combination of features found in the preferred embodiments disclosed herein.

These and other preferred embodiments of the present invention will be described in more detail below.

BRIEF DESCRIPTION OF THE DRAWINGS

The present invention will be better understood on reading the following detailed description of non-limiting embodiments thereof, and on examining the accompanying drawings, in which:

FIGS. 42A-42C show the tibial baseplate of FIG. 40A assembled with the keel of FIG. 41A.

FIG. 43 shows a cross-sectional view of the tibial implant shown in FIG. 42B taken along line 43-43 thereof.

FIG. 48 shows the tibial implant shown in FIG. 39 being assembled with a keel.

FIG. 49 shows a cross-sectional view of the tibial implant shown in FIG. 44.

FIG. 50 shows a magnified view of a portion of the tibial implant shown in FIG. 49.

DETAILED DESCRIPTION

Figure 1:
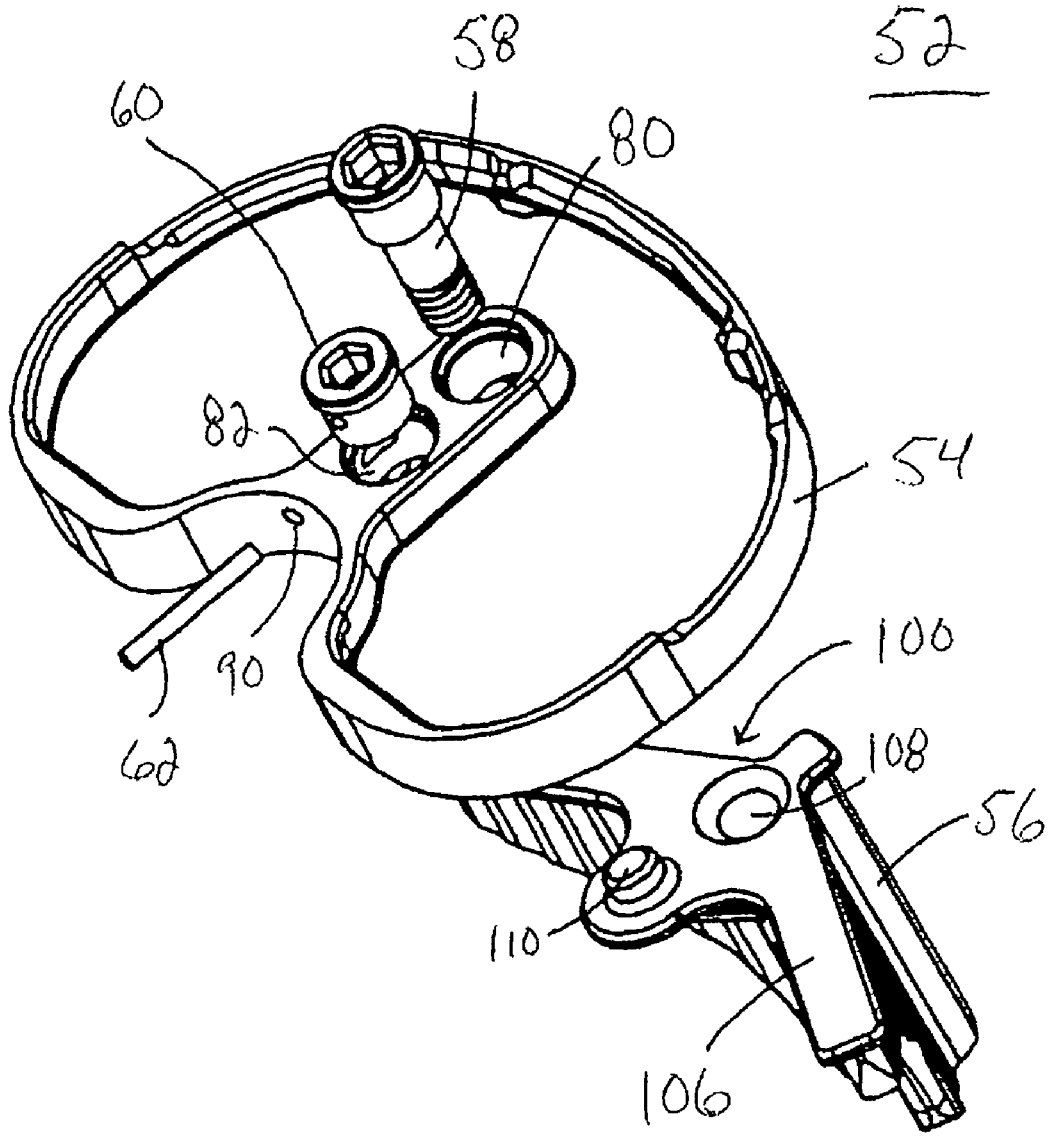
FIG. 1 shows a tibial implant, in accordance with certain preferred embodiments of the present invention.

Referring to FIG. 1, in accordance with certain preferred embodiments of the present invention, a tibial implant 52 includes a tibial baseplate 54, a keel 56, a locking element 58, a cam element 60 and a pin 62.

Figure 2:
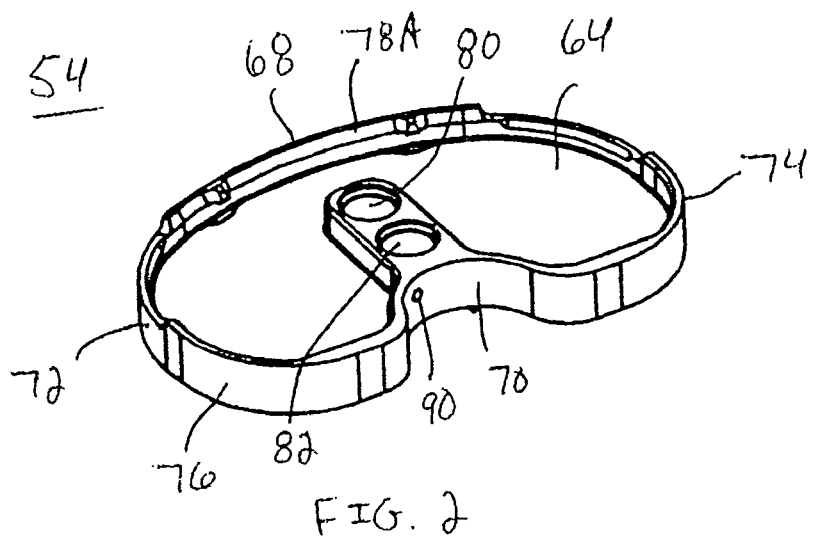
FIGS. 2-7 show a tibial baseplate for the tibial implant shown in FIG. 1.
Figure 3:
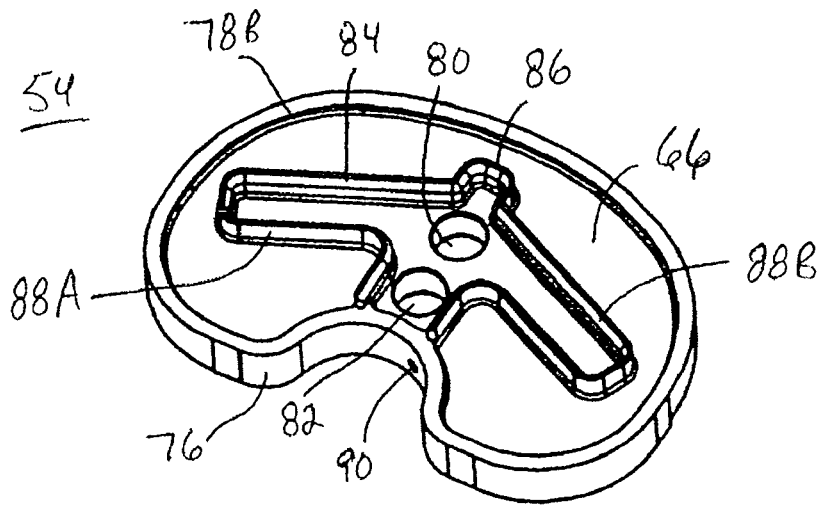

Referring to FIGS. 2 and 3, in certain preferred embodiments, the tibial baseplate 54 has an upper surface 64 and a lower surface 66. The tibial baseplate 54 preferably includes an anterior side 68, a posterior side 70, a first side 72 and a second side 74. The tibial baseplate 54 has a rim 76 that extends around an outer periphery thereof. The rim 76 includes a first section 78a that projects above the top surface 64 of the tibial baseplate and a second section 78b that projects below the bottom surface 66 of the tibial baseplate.

The tibial baseplate 54 includes a first opening 80 extending between the top surface 64 and the bottom surface 66, and a second opening 82 also extending between the top surface 64 and the bottom surface 66. In certain preferred embodiments, one or both of the first and second openings 80, 82 may be threaded. The tibial baseplate 54 also includes a barrier wall 84 that projects from the bottom surface 66 thereof. The barrier wall 84 has a central region 86 that surrounds the first and second openings 80, 82 and outer regions 88a, 88b that surround proximal ends of fins on a keel, as will be described in more detailed below.

Referring to FIGS. 2 and 3, the tibial baseplate 54 also includes a pin opening 90 that extends from the posterior side 70 of the baseplate and is in communication with the second opening 82. The pin opening 90 is adapted to receive the pin 62 shown in FIG. 1 for limiting movement and/or rotation of the cam element 60, as will be described in more detail below.

Figure 4:
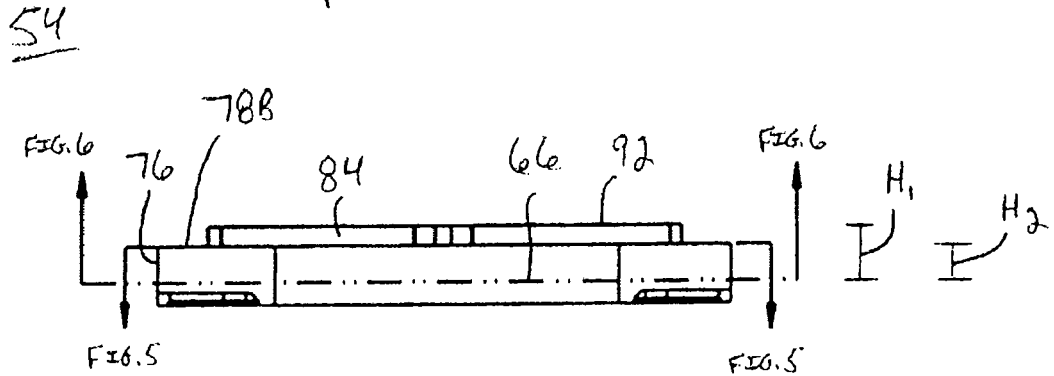

Referring to FIG. 4, the tibial baseplate 54 desirably includes barrier wall 84 that projects from the bottom surface 66 of the baseplate 54. The barrier wall 84 has a bottom edge 92 that defines a height $H_1$ from the bottom surface 66 of the tibial baseplate 54. The height $H_1$ of the barrier wall 84 is greater than the height $H_2$ of the second section 78b of the rim 76 that projects from the bottom surface 66 of the tibial baseplate. As a result, the barrier wall 84 has a greater height than the second section 78b of the rim 76 projecting from the bottom surface 66 to the tibial baseplate 54.

Figure 5:
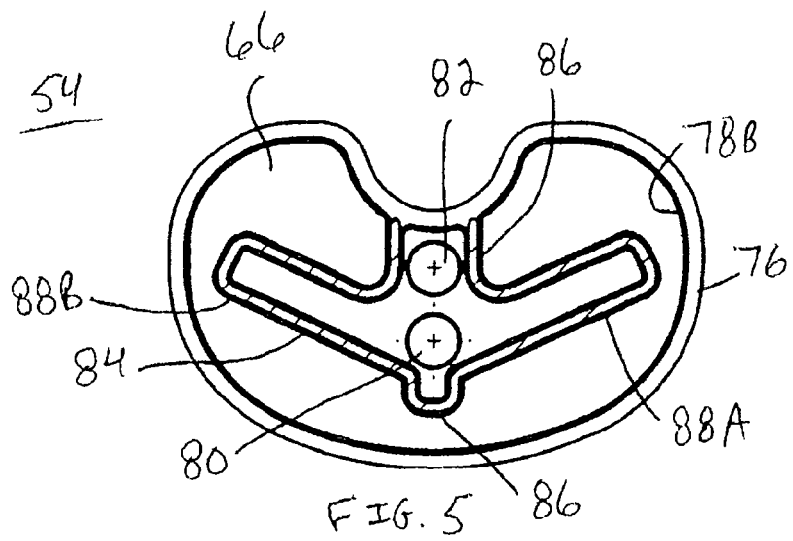

FIG. 5 shows the tibial baseplate 54 having a bottom surface 66, the first opening 80 and the second opening 82. The barrier wall 84 has a central section 86 that surrounds the first and second openings 80, 82 and outer sections 88a, 88b that surround other sections of the bottom surface 66. As noted above, the barrier wall 84 has a height that is greater than the height of the second section 78b of the rim 76.

Figure 6:
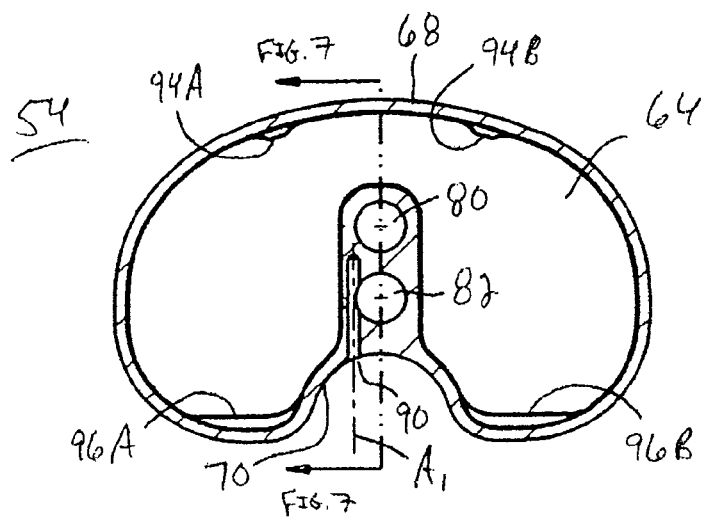

Referring to FIG. 6, the tibial baseplate 54 includes top surface 64 that is preferably adapted to receive a bearing insert (not shown). The tibial baseplate 54 includes anterior locking tabs 94a, 94b and posterior locking tabs 96a, 96b that preferably engage the bearing insert for holding the bearing insert in place over the top surface 64 of the baseplate 54. Tibial baseplate 54 includes pin opening 90 that extends from the posterior side 70 of the baseplate toward the anterior side 68 of the baseplate. The pin opening 90 preferably extends long an axis $A_1$.

Figure 7:
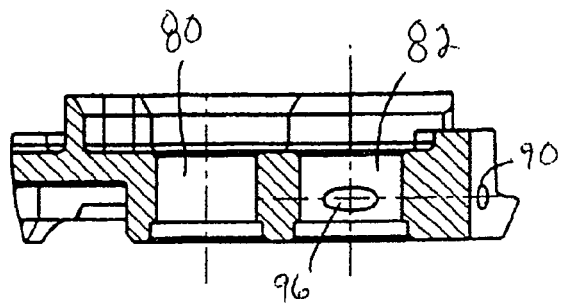

Referring to FIGS. 6 and 7, the pin opening 90 preferably intersects with an outer perimeter of the second opening 82. The intersection of the pin opening 90 and the second opening 82 forms a tangential opening 96.

Figure 8:
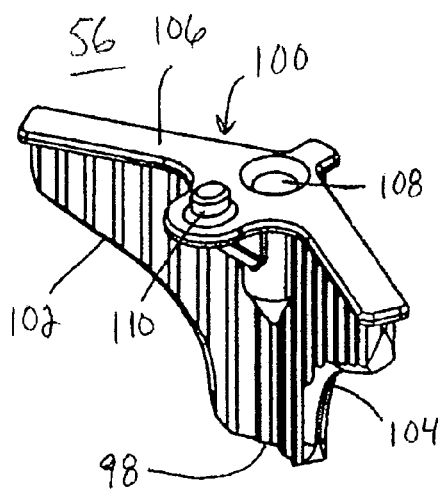
FIGS. 8-11 show a keel for the tibial implant of FIG. 1.
Figure 11:
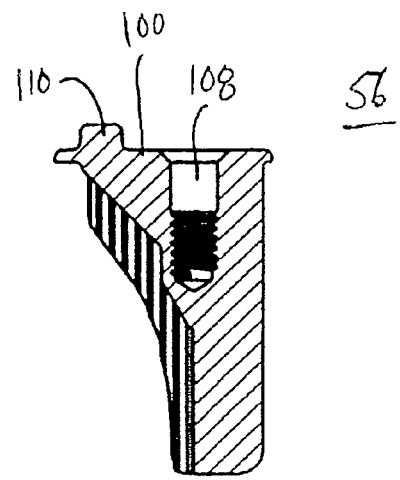
Figure 9:
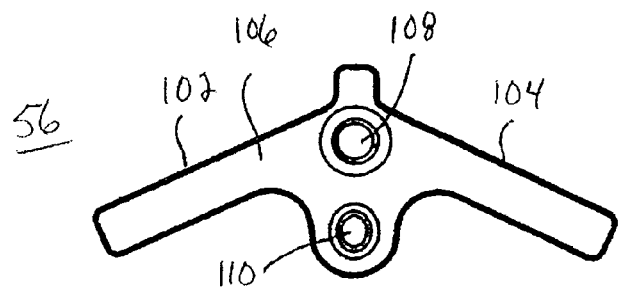
Figure 10:
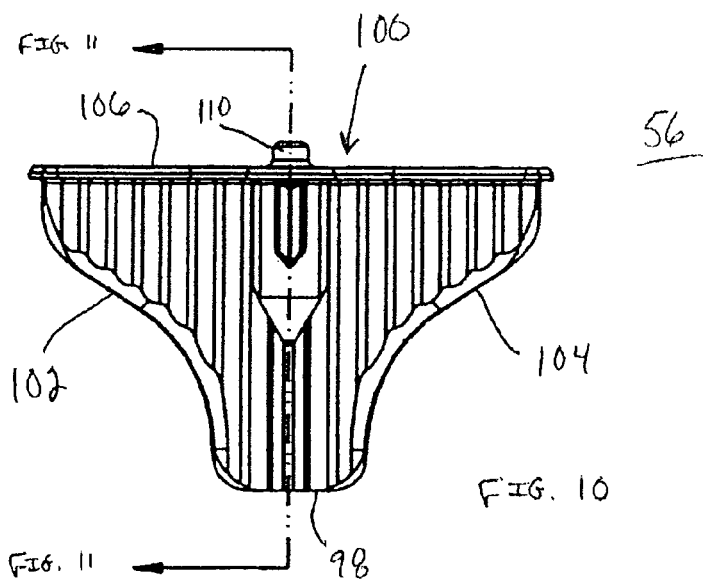
Figure 12A:
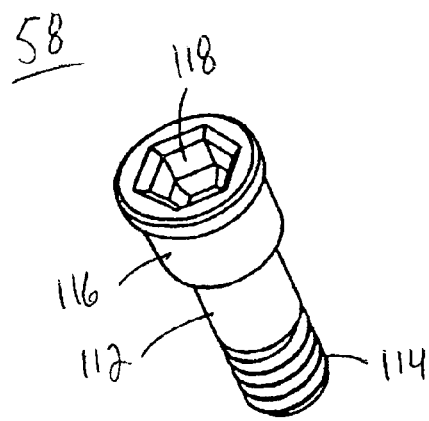
FIGS. 12A-12C and 13 show a fastener for the tibial implant of FIG. 1.
Figure 12B:
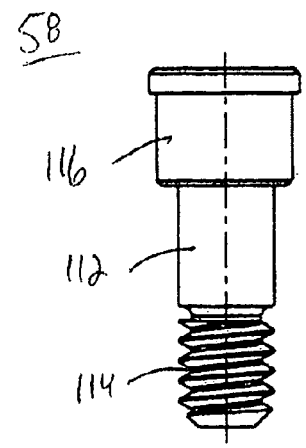
Figure 12C:
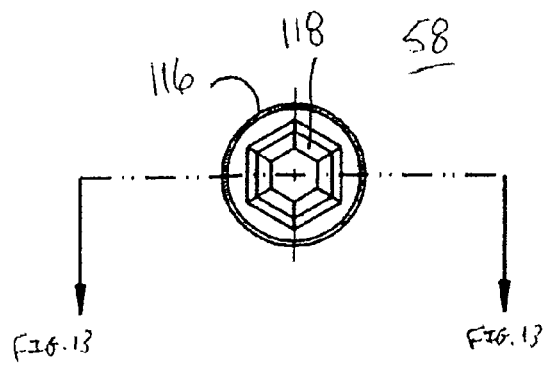
Figure 13:
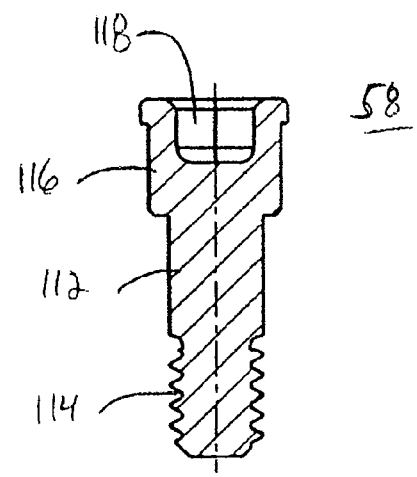
Figure 14A:
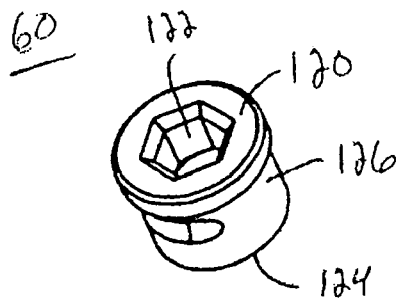
FIGS. 14A-14D show a cam element for the tibial implant of FIG. 1.
Figure 14B:
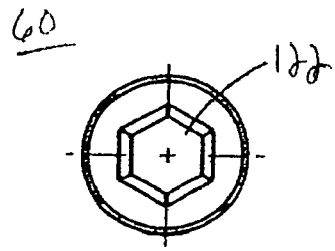
Figure 14C:
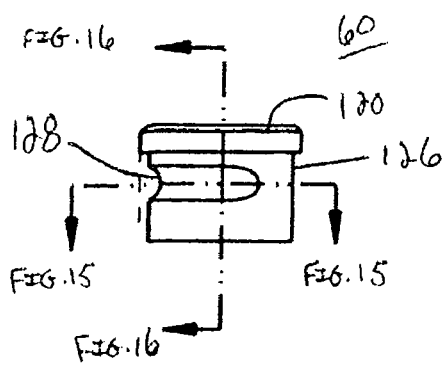

Referring to FIGS. 8-10, the tibial implant shown in FIG. 1 also preferably includes a keel 56 having a distal end 98, a proximal end 100, a first fin 102 and a second fin 104. The proximal end 100 of the keel 56 includes a bearing surface 106 that is adapted to abut against the bottom surface of the tibial baseplate. The keel 56 also desirably includes a female opening 108 having internal threads and a male projection 110 that is spaced from the female opening. The male projection 110 is preferable elongated and may have an oval, oblong or oblong-oval shape. Referring to FIG. 11, the keel 56 includes the threaded female opening 108 and the male projection 110 accessible at the proximal end 100 thereof.

Referring to FIGS. 12A-12C and FIG. 13, the tibial implant also preferably includes a fastener or locking element 58 with a shaft 112 having threads 114 and a head 116 including a recess 118 adapted to receive a driver such as a hex driver. As will be described in more detail below, after the tibial baseplate and the keel have been assembled together, the locking element 58 is insertible into the first opening of the baseplate and the female opening in the keel.

Referring to FIGS. 14A-14D, the tibial implant desirably includes a cam element 60 having an upper end 120 with a tool receiving recess 122 and a lower end 124. The cam element 60 desirably includes a shaft 126 that extends between the upper end 120 and the lower end 124. The outer surface of the shaft 126 has a radial groove 128 formed in a section thereof. The radial groove preferably extends in a direction that is substantially perpendicular to a longitudinal axis extending between the upper and lower ends 120, 124 of the cam element 60. In certain preferred embodiments, the groove extends about 90° around the outer perimeter of the shaft 126. In other preferred embodiments, the groove may extend more or less than 90° around the perimeter of the shaft.

Figure 15:
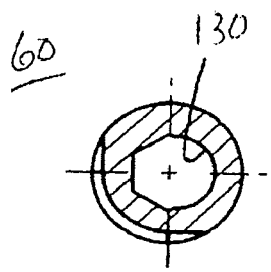
FIG. 15 shows a cross-sectional view of the cam element shown in FIG. 14C taken along line 15-15 thereof.
Figure 16:
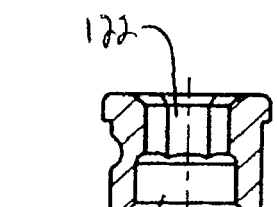
FIG. 16 shows a cross-sectional view of the cam element of FIG. 14C taken along line 16-16 thereof.
Figure 14D:
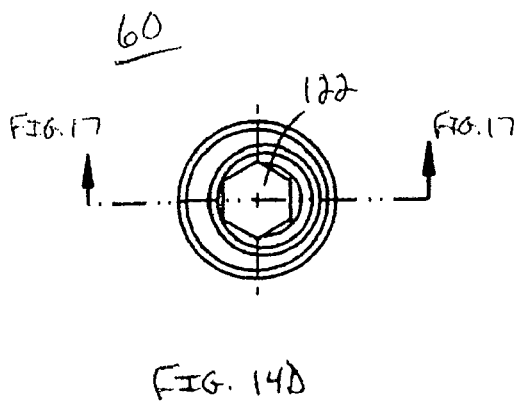
Figure 17:
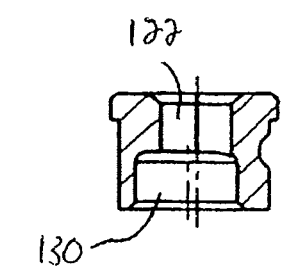
FIG. 17 shows a cross-sectional view of the cam element shown in FIG. 14D taken along line 17-17 thereof.

FIG. 15 shows an asymmetrical opening 130 that is located adjacent the lower end 124 of the cam element 60. Referring to FIG. 16, along a first axis, the opening 130 is symmetrical about the tool opening 122. Along a second axis, however, the opening 130 is asymmetrical relative to the tool opening 122. After the baseplate 54 and the keel 56 are assembled together and the cam element 60 is inserted in the second opening 82, the cam element is rotated for applying a camming force to the baseplate. During rotation of the cam element, the asymmetrical opening 130 bears against the oval-shaped male projection 110 (FIG. 1) at the proximal end of the keel for generating the camming force.

Although the present invention is not limited by any particular theory of operation, it has been determined that the cam element generates a tighter fit and more locking force between the tibial baseplate and the keel. After the locking element is tightened, the baseplate and the keel are secured together and may not be pulled apart from one another along a longitudinal axis of the locking element. Thus, the baseplate and the keel may not move "vertically" relative to one another. However, the baseplate and the keel may still move "horizontally" relative to one another, i.e., in a direction that is parallel to a plane defined by the upper surface of the tibial baseplate. Thus, after the locking element has been fully tightened to limit vertical movement of the baseplate relative to the keel, the cam element is utilized to move the baseplate "horizontally" relative to the keel to further enhance the locking force between the baseplate and the keel. Although the cam element described in this embodiment is rotatable, it is contemplated that other types of cam elements that are not rotatable may be used as well.

Figure 18A:
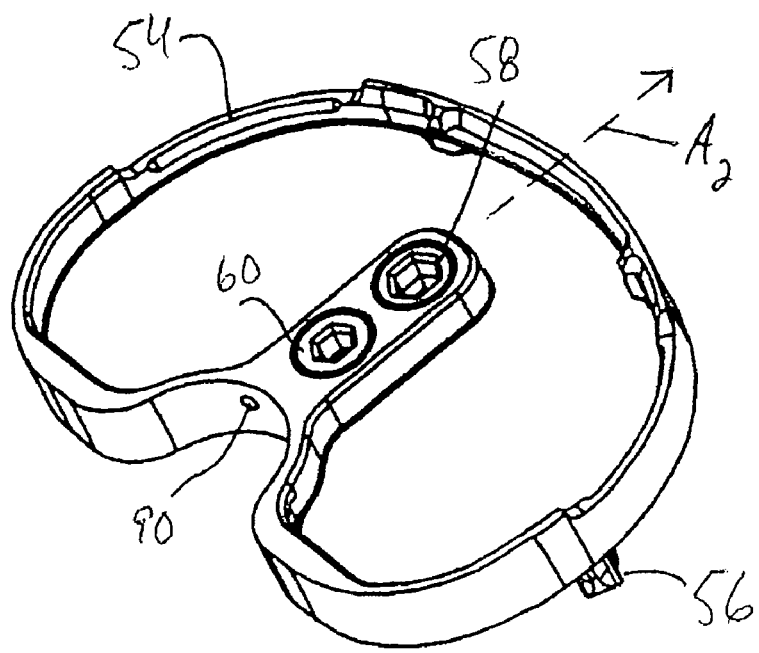
FIGS. 18A and 18B show the tibial implant of FIG. 1 after being partially assembled.
Figure 18B:
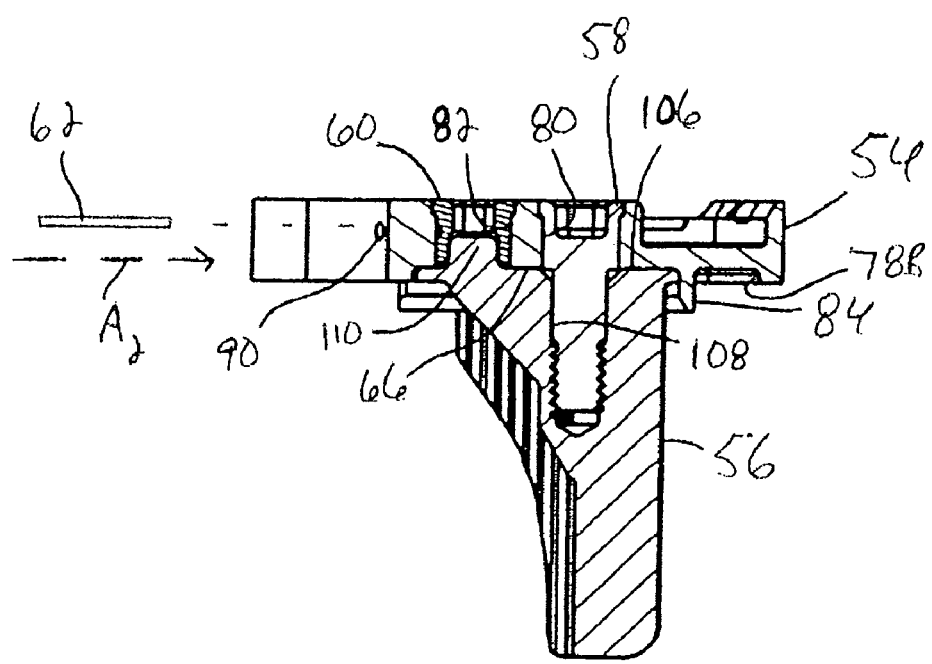

Referring to FIGS. 1 and 18a, after keel 56 has been anchored in bone, such as the bone at the end of a tibia, the proximal end of the keel is preferably accessible for mating with the tibial baseplate 54. The bearing surface 106 of the keel 56 is preferably abutted against the bottom surface 66 of the tibial baseplate 54, with the first opening 80 in the tibial baseplate 54 aligned with the threaded female opening 108 in the keel and the second opening 82 of the baseplate aligned with the male projection 110. The locking element 58 is preferably inserted into the first opening 82 and threaded into the threads at the lower end of the threaded female opening 108 in the keel. As the locking element 58 is rotated, the threads of the locking element mesh with the threads of the female opening 108 for securing the tibial baseplate 54 to the keel 56. The barrier wall 84, which surrounds the fins at the proximal end of the keel, has a height that projects below the lower rim extension 78b at the periphery or perimeter of the tibial baseplate 54.

In order to enhance locking force between the tibial baseplate 54 and the keel 56, the cam element 60 is introduced into the second opening 82 of the tibial baseplate 54. As the cam element 60 is rotated, a side wall of the asymmetrical opening 130 engages the male projection 110 on the keel 56 for urging the tibial baseplate 54 to move along the axis $A_2$ relative to the keel 56. The movement along the axis $A_2$, due to the camming force applied by the cam element, further enhances the locking force generated between the tibial baseplate 54 and the keel 56. In order to prevent the cam element 60 from over-rotating during assembly, a pin 62 is inserted into pin opening 90. The pin is advanced to the tangential opening 96 (FIG. 7) in the baseplate where it engages the groove 128 (FIGS. 14a-14B) in the cam element 60. The pin 62 is preferably held in place in the tangential opening 96, such as by using a spot weld. As a result of the pin engaging the groove 128, the cam element 60 cannot rotate in a direction that would loosen the camming force, which insures that the camming force remains exerted upon the tibial baseplate 54.

Referring to FIG. 1, during assembly of the implant 52, the cam element 60 is inserted into the second opening 82 in the tibial baseplate 54. The pin 62 is inserted into the tangential opening 90 and advanced until the pin engages the groove 128 in the cam element 60. A spot weld or other securing composition may be used to hold the pin 62 in the tangential opening 90 and in engagement with the groove in the cam element. The above steps preferably take place before surgery, and more preferably before the implant reaches a surgeon. As a result, during surgery, the surgeon will only have to handle three different parts, namely the tibial baseplate 54 (including the pin 62 and the cam element 60), the bone engaging element 56 and the screw fastener 58.

Figure 19:
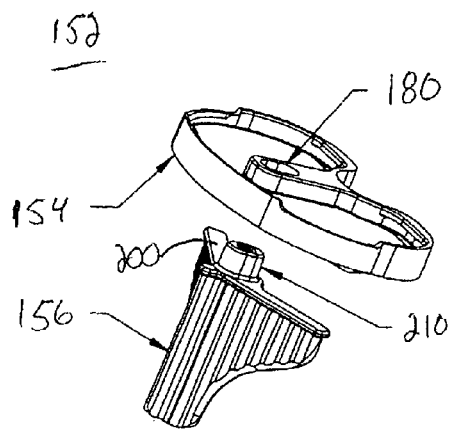
FIG. 19 shows a tibial implant, in accordance with another preferred embodiment of the present invention.

Referring to FIG. 19, in another preferred embodiment of the present invention, a tibial implant assembly 152 includes a tibial baseplate 154 having a tapered opening 180 extending therethrough and a keel 156 having a tapered projection 210 extending from a proximal end 200 thereof.

Figure 20A:
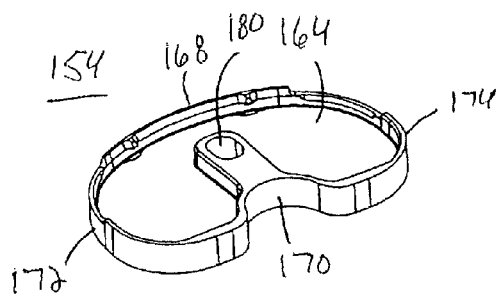
FIGS. 20A-20D show a tibial baseplate for the tibial implant shown in FIG. 19.
Figure 20B:
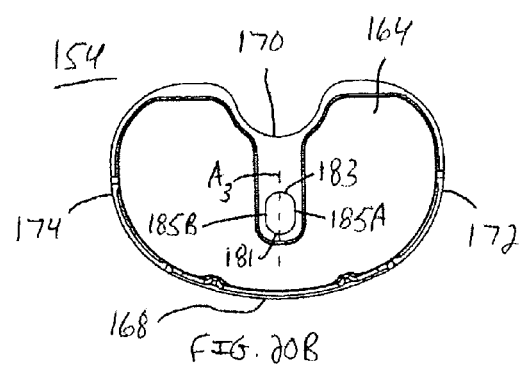
Figure 20C:
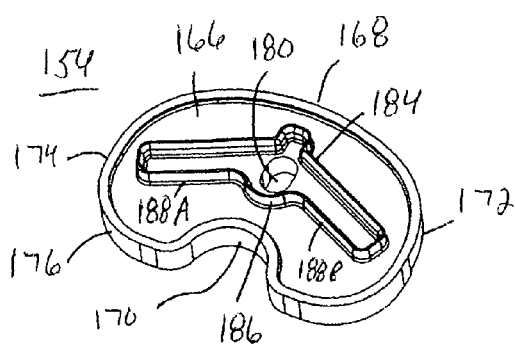
Figure 20D:
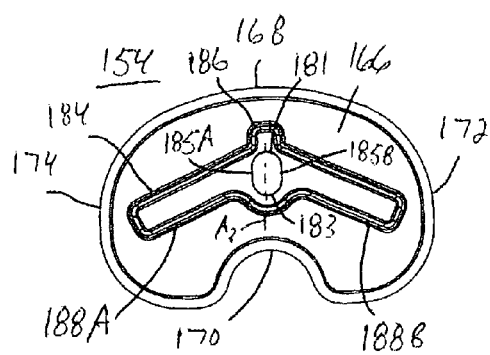

Referring to FIGS. 20A-20D, the tibial baseplate 154 has an upper surface 164 and a bottom surface 166. The tibial baseplate also preferably has an anterior side 168, a posterior side 170, a first side 172 and a second side 174. The tibial baseplate 154 desirably includes the tapered opening 180 extending between the upper surface 164 and the bottom surface 166 thereof. In certain preferred embodiments, the tapered opening has an oblong-oval shape. Referring to FIGS. 20B and 20D, the oblong-oval shaped tapered opening 180 has a longitudinal axis $A_3$ with a first curved surface 181 at a leading end of the opening and a second curved surface 183 at a trailing end of the opening. The tapered opening also includes opposing flat sides 185a, 185b that extend between the first and second curved surfaces 181, 183. In certain preferred embodiments, the circumference of the tapered opening 180 is smaller at the upper end of the opening and larger at the bottom end of the opening. In this embodiment, the size of the opening becomes greater as it extends between the top surface 164 of the baseplate and toward the bottom surface 166 of the baseplate. In other preferred embodiments, however, the tapered opening may be larger at the upper end and smaller at the lower end thereof. In certain preferred embodiments, the tapered opening may have an oval shape.

Referring to FIGS. 20C and 20D, the tibial baseplate 154 also preferably includes a barrier wall 184 that projects from the bottom surface 166 of the baseplate. The barrier wall 184 has a height that is greater than the portion of the rim 176 that projects below the bottom surface 166 of the baseplate 154. The barrier wall 184 desirably includes a central region 186 that surrounds the tapered opening 180 and side regions 188a, 188b that are adapted to surround the proximal ends of the fins on the keel 156, as will be described in more detail below.

Figure 21A:
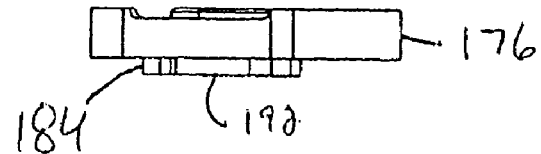
FIG. 21A shows a side elevational view of the tibial baseplate shown in FIG. 20A.
Figure 21B:
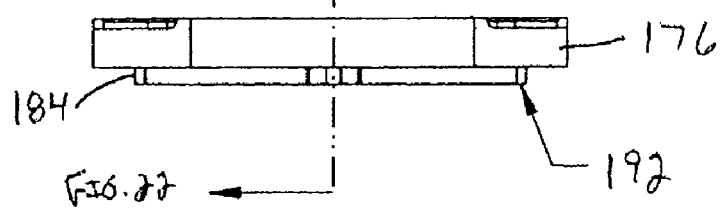
FIG. 21B shows a front elevational view of the tibial baseplate shown in FIG. 20A.

Referring to FIGS. 21A and 21B, the barrier wall 184 has a lower edge 192 that projects beyond the lower edge of the rim 176 of the tibial baseplate 154. Although the present invention is not limited by any particular theory of operation, it is believed that the height of the barrier wall 184 prevents bone cement and/or adhesive used in the procedure from getting inside the region of the baseplate bounded by the barrier wall. As is well-known to those skilled in the art, the presence of cement or adhesive at the junction between the proximal end of the fins on the keel and the bottom surface of the tibial baseplate may eventually result in the bone cement or adhesive migrating into contact with the barrier insert secured over the top surface of the tibial baseplate, which may damage the barrier insert. Thus, in order to prevent the bone cement or adhesive from migrating into contact with the barrier insert, the barrier wall 184 is utilized to provide a reliable border/barrier. The height of the barrier wall 184 relative to the rim 176 further enhances the level of prevention/protection.

Figure 22:
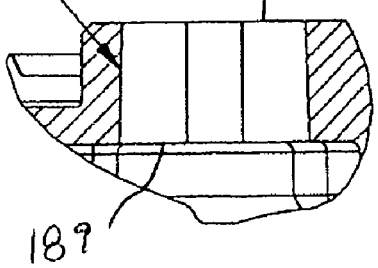
FIG. 22 shows a partial cross-sectional view of the tibial baseplate shown in FIG. 20A.
Figure 23B:
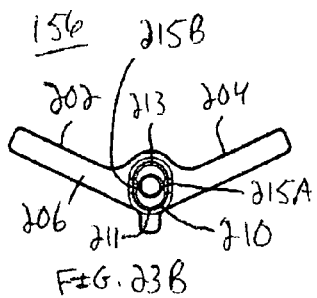
FIGS. 23A-23D show a keel for the tibial implant shown in FIG. 19.
Figure 23A:
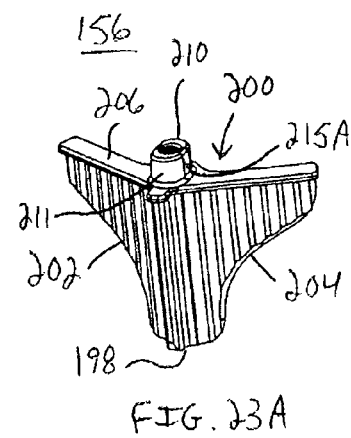

Referring to FIG. 22, the baseplate 154 preferably includes a tapered opening 180 having an upper end 187 and a lower end 189. The tapered opening 180 tapers outwardly between the upper end 187 and the lower end 189. In other preferred embodiments, however, the tapered opening may become smaller between the upper and lower ends 187, 189.

Referring to FIGS. 23A-23D, the tibial implant also desirably includes a keel 156 having a distal end 198 and a proximal end 200. The keel 156 also includes a first fin 202 and a second fin 204 extending between the distal and proximal ends 198, 200. The proximal end 200 of the fins define a bearing surface 206 that is adapted to abut against the bottom surface 266 of the tibial baseplate 154 (FIG. 20C). The keel 156 also includes a male projection 210 extending from the proximal end 200 of the keel. The male projection 210 is tapered and preferably has an oblong-oval shape. The outer surface of the male projection 210 preferably has a first curve 211 at a leading end of the projection and a second curve to 213 at a trailing end of the projection. The projection is elongated between the first and second curves 211, 213. The projection 210 also preferably includes opposing flat side surface 215a, 215b. The flat side surfaces may be parallel to one another or may be tapered relative to one another.

Figure 24:
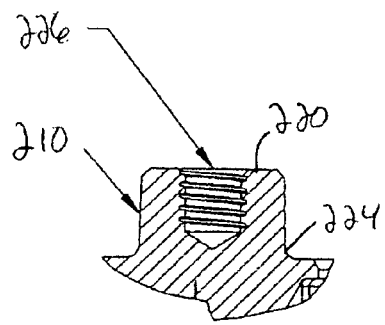
FIG. 24 shows a partial cross-sectional view of the keel shown in FIG. 23A.
Figure 23C:
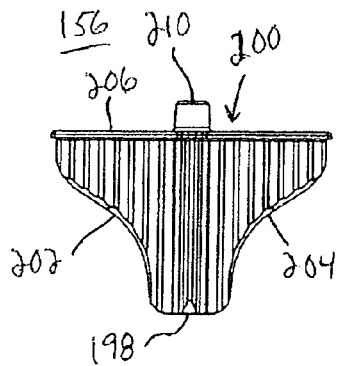
Figure 23D:
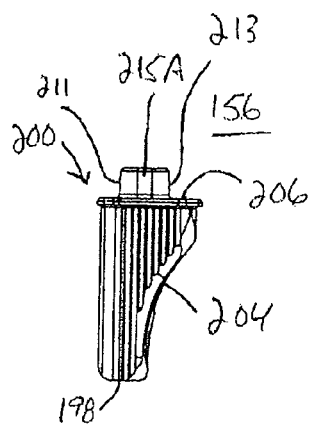

Referring to FIG. 24, the tapered male projection 210 desirably has an upper end 220 and a lower end 224, with a threaded opening 226 extending from the upper end toward the lower end. The male projection 210 preferably tapers outwardly between the upper and lower ends so that the circumference of the projection at the upper end 220 is less than the circumference of the projection at the lower end 224. In other preferred embodiments, however, the projection may taper inwardly between the upper and lower ends. In still other preferred embodiments, the tapered projection does not have a threaded opening and the baseplate and bone engaging element are held together by only a press fit of the tapered projection and the tapered opening.

Figure 25A:
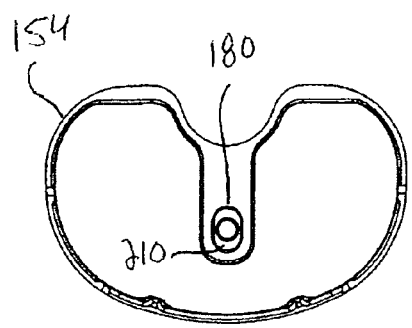
FIGS. 25A-25C show the tibial baseplate of FIG. 20A being assembled with the keel of FIG. 23A.
Figure 25B:
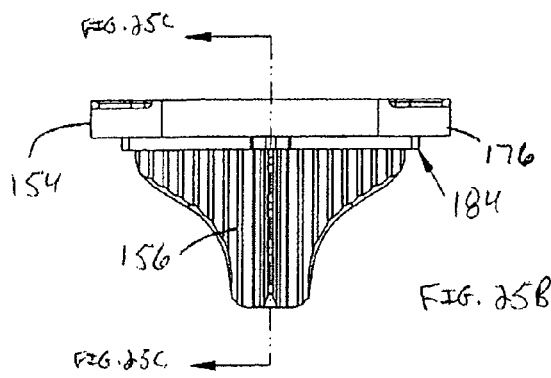
Figure 25C:
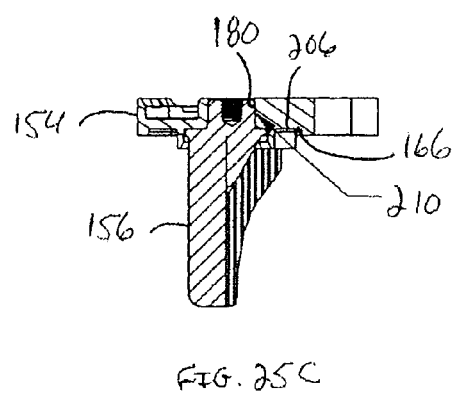
Figure 26:
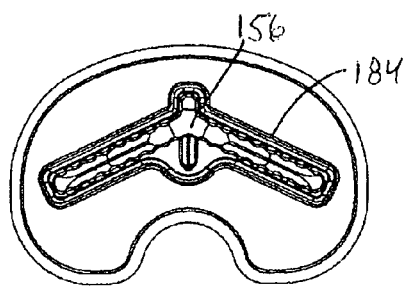
FIG. 26 shows a bottom plan view of the tibial implant assembly shown in FIG. 25B.

Referring to FIGS. 19 and 25A-25C, the tibial implant is assembled together by abutting the bottom surface 166 of the tibial baseplate 154 against the proximal end of the keel 156. As shown in FIGS. 19 and 25A, the male projection 210 is placed in alignment with the opening 180 in the tibial baseplate, and inserted into the opening 180 as shown in FIG. 25C. During assembly, the bearing surface 206 at the proximal end of the keel 156 engages the bottom surface 166 of the tibial baseplate, as shown in FIGS. 25B and 26, with the barrier wall 184 extending around the keel 156. In addition, as shown in FIG. 25B, the lower edge of the barrier wall 184 projects below the rim 176 surrounding the perimeter of the baseplate 154.

Figure 27B:
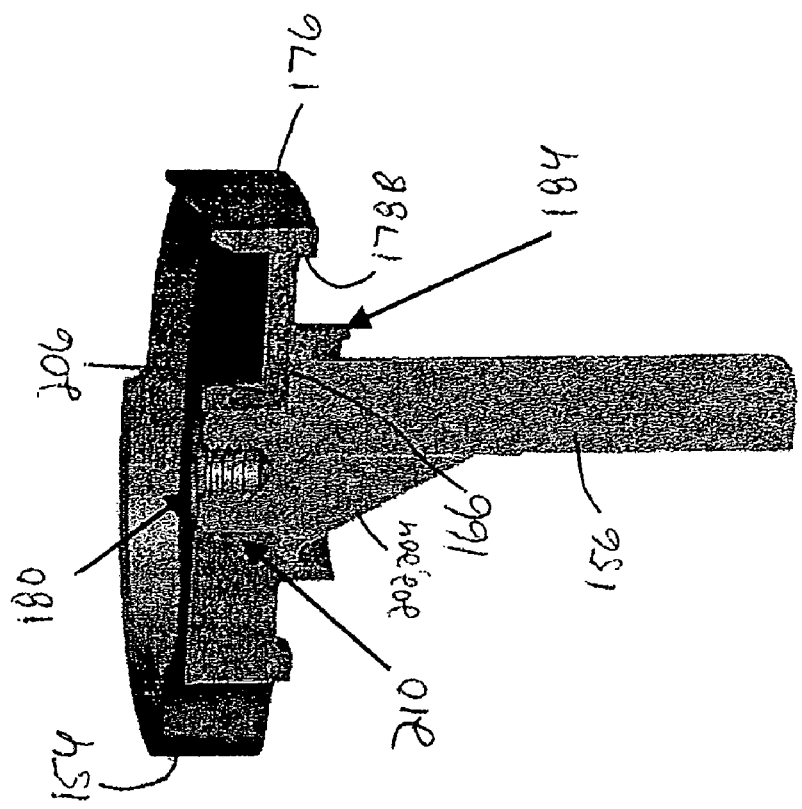
FIGS. 27A-27B show assembly of the tibial implant shown in FIG. 19.
Figure 27A:
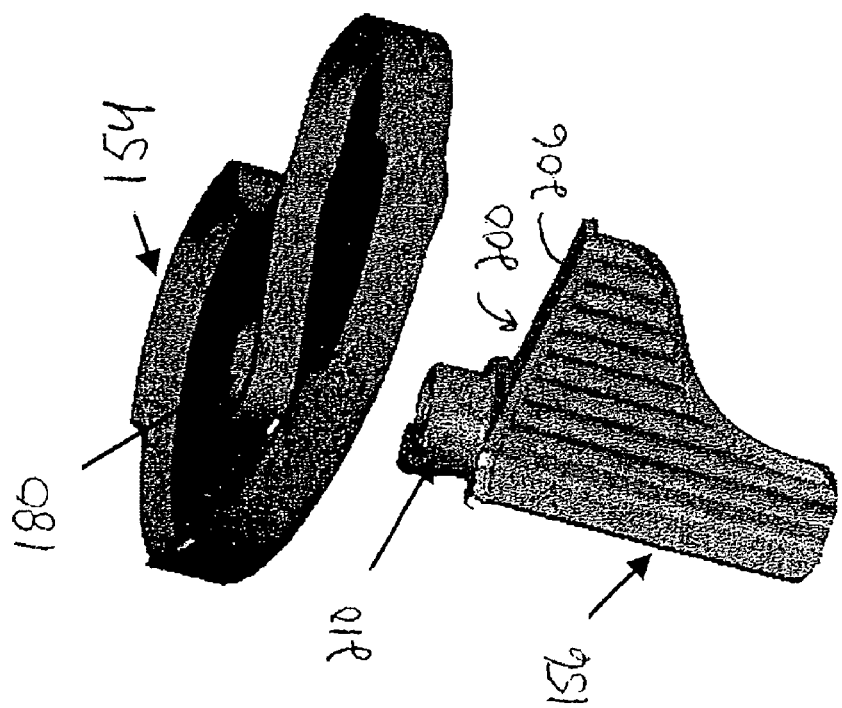

FIGS. 27A and 27B show other views of the tibial baseplate 154 being assembled with the keel 156. The opening 180 in the baseplate 154 is aligned with the male projection 210 at the proximal end 200 of the keel 156. During assembly, the male projection is inserted into the opening 180. In addition, the bearing surface 206 at the proximal end of the keel is abutted against the bottom surface 166 of the tibial baseplate 154, with the fins 202, 204 of the keel 156 being surrounded by the barrier wall 184. In order to secure the baseplate and the keel together, a locking element may be inserted into the opening 180 in the baseplate 154. The locking element may have threads for being threaded into the female threads in the male projection 210.

Figure 28:
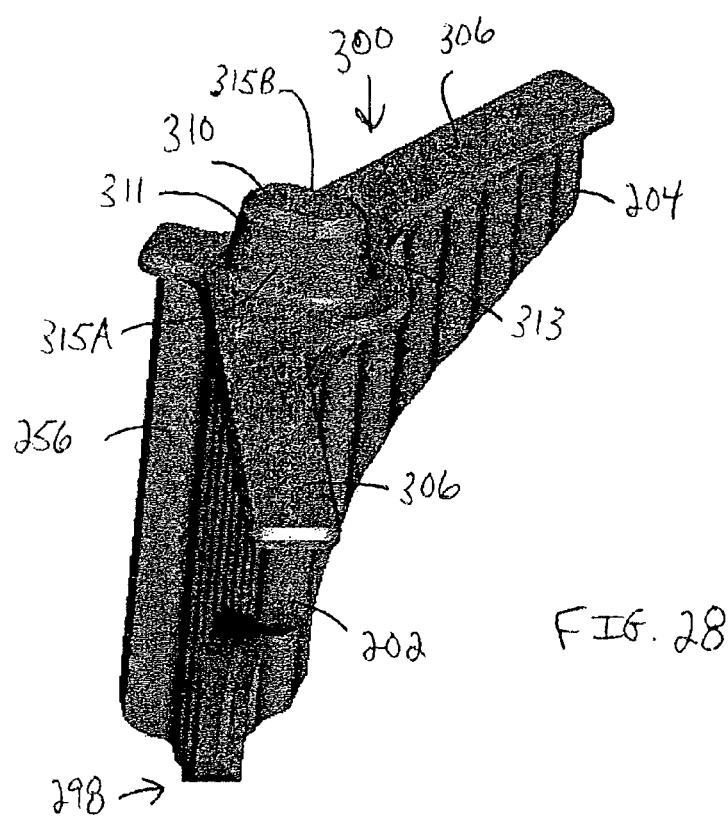
FIG. 28 shows a perspective view of a keel for a tibial implant assembly, in accordance with another preferred embodiment of the present invention.
Figure 29:
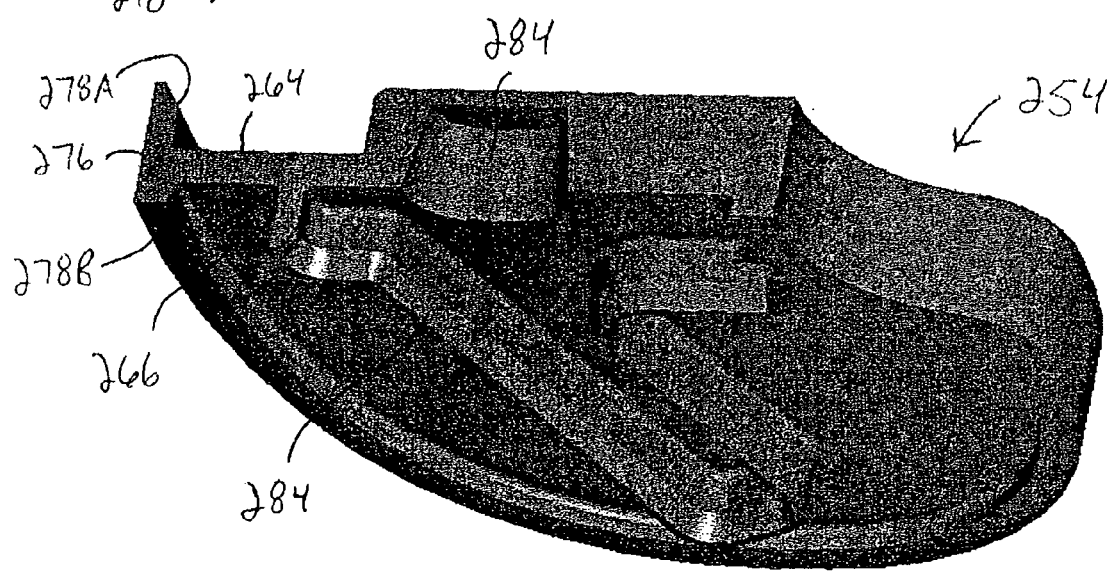
FIG. 29 shows a cross-sectional view of a tibial baseplate, in accordance with further preferred embodiments of the present invention.
Figure 30:
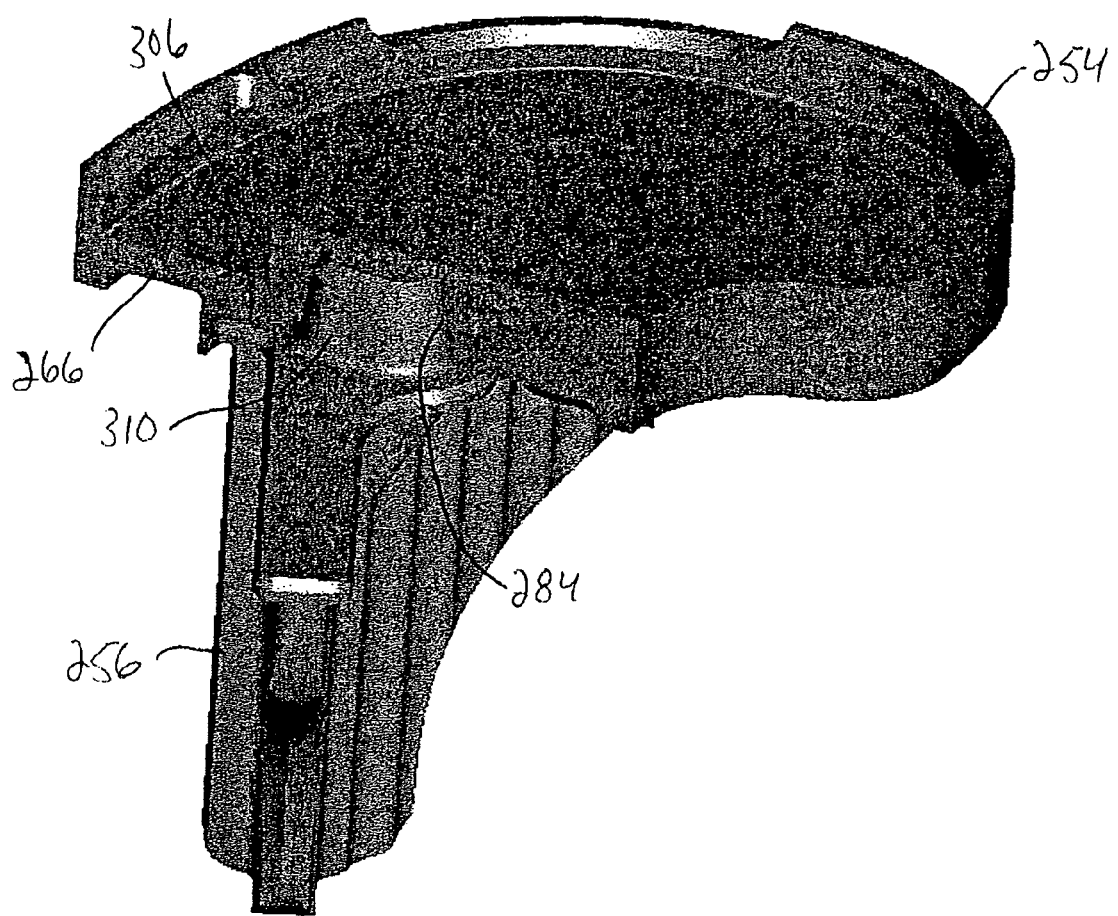
FIG. 30 shows the tibial baseplate of FIG. 29 in cross-section assembled with the keel of FIG. 28.

FIGS. 28-30 show a tibial implant, in accordance with another preferred embodiment of the present invention. Referring to FIG. 28, the tibial implant includes a keel 256 having a distal end 298 and a proximal end 300. The keel includes fins 202, 204 extending between the distal end 298 and the proximal end 300. The proximal end includes a bearing surface 306 that extends along an upper edge of the fins 202, 204. The proximal end 300 of keel 256 also includes a tapered male projection 310. The tapered male projection 310 preferably has an oblong-oval shape. The projection is preferably elongated with a leading end defining a first curve 311, a trailing end defining a second curve 313 and first and second flat sides 315a, 315b extending between the first and second curves 311, 313.

Referring to FIG. 29, the keel is adapted for assembly with a tibial baseplate 254 having an upper surface 264 and a bottom surface 266. The tibial baseplate also includes a rim 276 extending around a perimeter of the baseplate with a first section 278a of the rim 276 projecting above the upper surface 264 of the baseplate and a second section 278b of the rim 276 projecting below the bottom surface 266 of the baseplate. The tibial baseplate 254 also includes a barrier wall 284 that projects from the bottom surface 266. The barrier wall 284 preferably has a height that is greater than the height of the second section 278b of the rim 276. In other words, a lower edge of the barrier wall 284 projects below the lower edge of the second section 278b of the rim 276. The tibial baseplate 254 also preferably includes a tapered female opening 284, which is a blind opening and is not accessible from the upper surface 264 of the baseplate 254. The tapered female opening is preferably oblong-oval in shape and generally matches the shape and taper of the male projection 310 shown in FIG. 28.

Referring to FIG. 30, the tibial baseplate 254 is assembled with the keel 256 by aligning the tapered male projection 310 with the tapered female opening 284 at the bottom of the baseplate. The male projection 310 is inserted into the female opening 284 and advanced until fully seated therein. As the male projection 310 advances into the female opening 284, the bearing surface 306 at the proximal end of the keel preferably abuts against the bottom surface 266 of the tibial baseplate 254. After assembly, the tibial baseplate 254 and the keel 256 are held together by a taper lock formed between the tapered male projection 310 and the tapered female opening 284.

Figure 31:
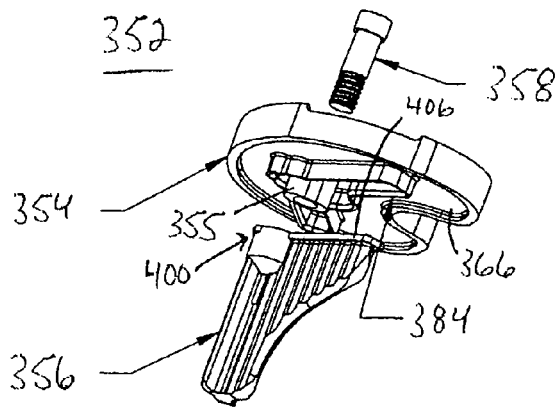
FIG. 31 shows a tibial implant, in accordance with still further preferred embodiments of the present invention.

Referring to FIG. 31, a tibial implant 352 in accordance with another preferred embodiment of the present invention includes a tibial baseplate 354 having a tapered male projection 355 that is insertible into a tapered female projection located at a proximal end 400 of a keel 356. The tibial baseplate 354 includes a barrier wall 384 that projects from a bottom surface 366 of the baseplate 354. The barrier wall 384 is shaped and sized to surround the male projection 355 and to receive the bearing surface located at the proximal end of the keel 356. After the baseplate 354 and the keel 356 are assembled together, a locking element 358 may be passed through the opening in the male projection 355 to secure the baseplate 354 and the keel 356 together.

Referring to FIGS. 32A-32D, the tibial baseplate 354 includes an upper surface 364, a bottom surface 366 and an opening 380 extending between the upper surface 364 and the bottom surface 366. The upper surface 364 is sized and shaped to receive a bearing insert (not shown).

Figure 32A:
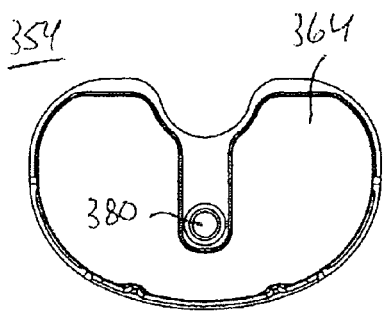
FIGS. 32A-32D show a tibial baseplate for the tibial implant of FIG. 31.
Figure 32B:
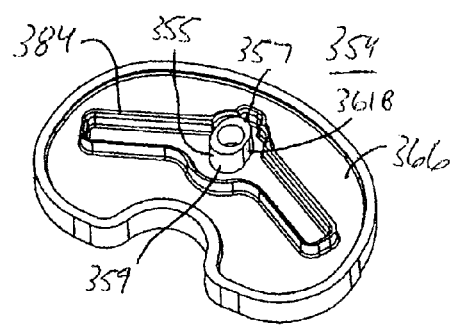
Figure 32C:
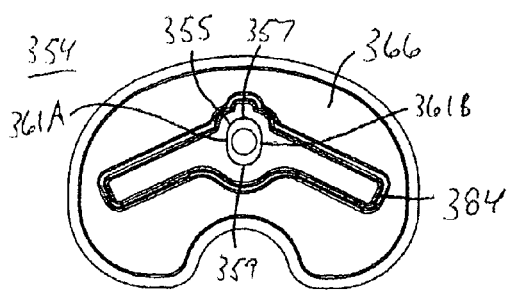

Referring to FIGS. 32B and 32C, the tibial baseplate also desirably includes a tapered male projection 355 that projects from the bottom surface 366 thereof. The tapered male projection 355 includes a leading end defining a first curve 357, a tailing end defining a second curve 359 and opposing flat sides 361a, 361b. The tibial baseplate 354 also includes a barrier wall 384 that projects from the bottom surface 366 thereof. The barrier wall 384 generally mirrors the shape of the proximal end of the keel 356 (FIG. 31) and surrounds the male projection 355.

Figure 32D:
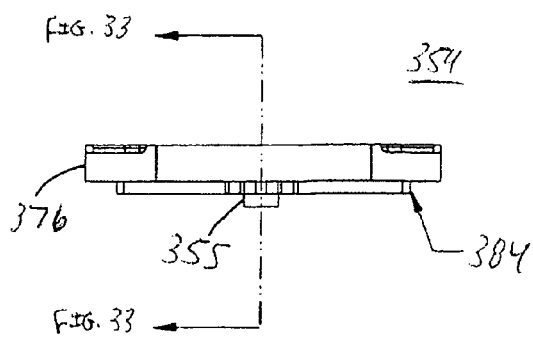
Figure 33:
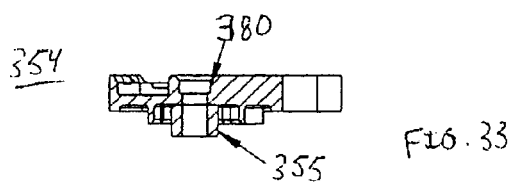
FIG. 33 shows a cross-sectional view of the tibial baseplate shown in FIG. 32D taken along line 33-33 thereof.
Figure 34A:
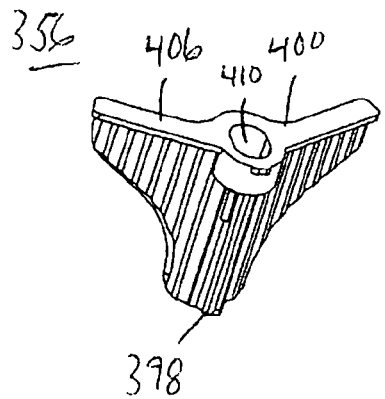
FIGS. 34A-34D show a keel for the tibial implant shown in FIG. 31.
Figure 34B:
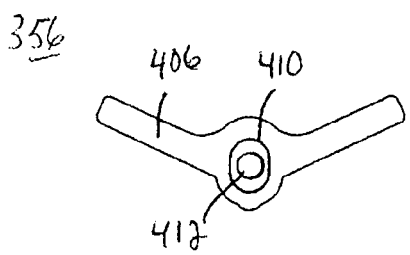
Figure 34C:
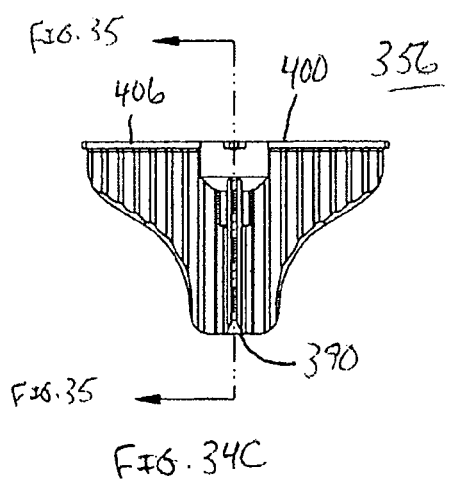
Figure 35:
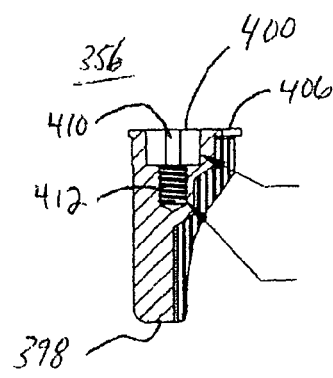
FIG. 35 shows a cross-sectional view of the keel of FIG. 34C taken along line 35-35 thereof.
Figure 34D:
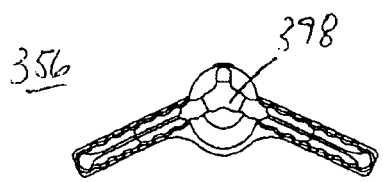

Referring to FIGS. 32D and 33, the male projection 355 tapers inwardly between the upper surface 364 and the lower surface 366 of the baseplate 354. The male projection 355 is surrounded by the barrier wall 384, which projects below the lower edge of rim 376. As shown in FIG. 33, the opening 380 accessible at the upper surface 364 of the baseplate 354 extends through the tapered male projection 355.

Figure 36A:
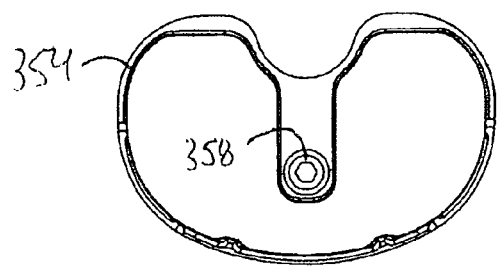
FIGS. 36A-36C show the tibial baseplate of FIG. 32A assembled with the keel of FIG. 34A.
Figure 36B:
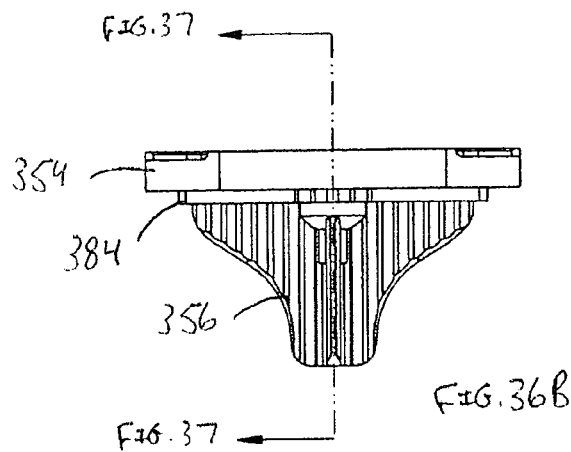
Figure 37:
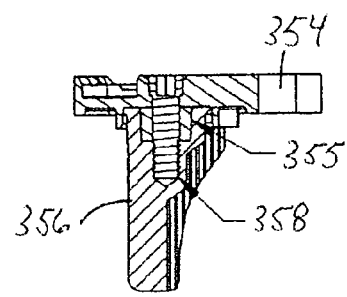
FIG. 37 shows a cross-sectional view of the tibial implant of FIG. 36B taken along line 37-37 thereof.
Figure 36C:
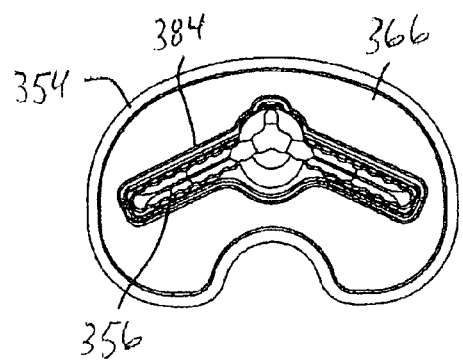

Referring to FIGS. 34A-34D and 35, the tibial implant also desirably includes a keel 356 having a distal end 398 and a proximal end 400 including a bearing surface 406. The keel 356 includes a tapered female opening 410 having internal threads 412. The internal threads are preferably provided at a lower end of the opening 410. The tapered female opening 410 has an oblong-oval shape that matches the oblong-oval shape of the male projection at the underside of the tibial baseplate. Referring to FIGS. 31 and 36A, when assembling the tibial baseplate 354 with the keel 356, the bearing surface 406 at the proximal end 400 of the keel 356 is aligned with the area bounded by the barrier wall 384. In addition, the female opening 410 is aligned with the male projection 355, and the male projection 355 is inserted into the female opening 410. After assembly, the barrier wall 384 surrounds the proximal end of the keel. After the male projection is seated into the female opening, the locking element 358 is inserted into the opening 380 in the baseplate 354. The threads of the locking element are threaded into the female threads of the female opening 410 for securing the baseplate and the keel together.

Figure 38B:
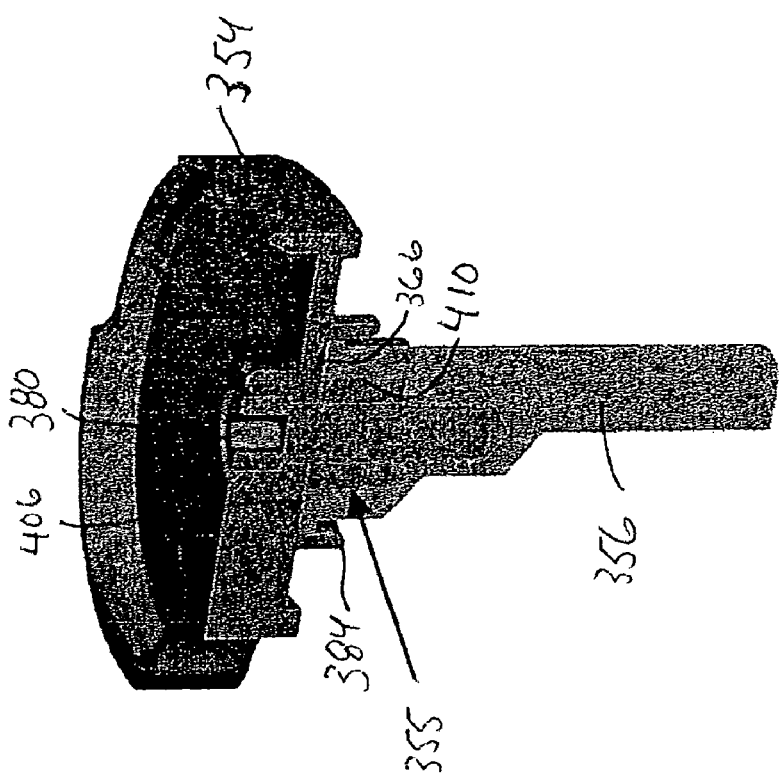
FIGS. 38A and 38B show the tibial baseplate of FIG. 32A being assembled with the keel of FIG. 34A, with FIG. 38B being a cross-sectional view.
Figure 38A:
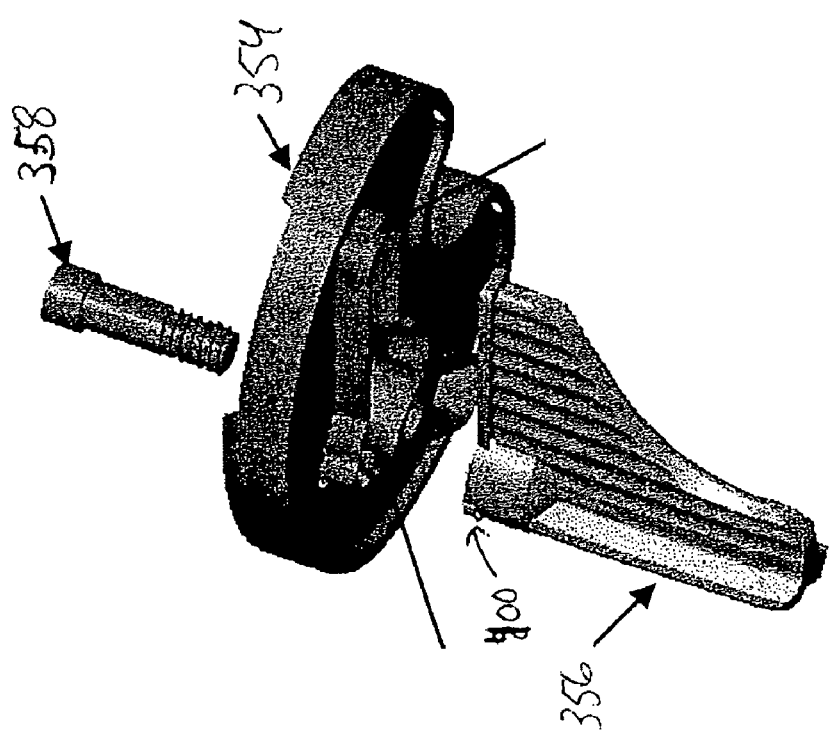

Referring to FIGS. 38A and 38B, the tibial baseplate 354 is assembled with the proximal end 400 of keel 356. During assembly, the male projection 355 is captured within the female opening 410 and the bearing surface 406 at the proximal end of the keel 356 abuts against the bottom surface 366 of the tibial baseplate 354. The tapered male projection 355 forms a taper lock with the tapered female opening 410. In addition, the barrier wall 384 surrounds the proximal end of the keel 356. The locking element 358 is then passed through the opening 380 in the baseplate 354 and into the threaded female opening 410. The threads on the locking elements 380 mesh with the threads in the female opening for securing the baseplate 354 with the keel 356.

Figure 39:
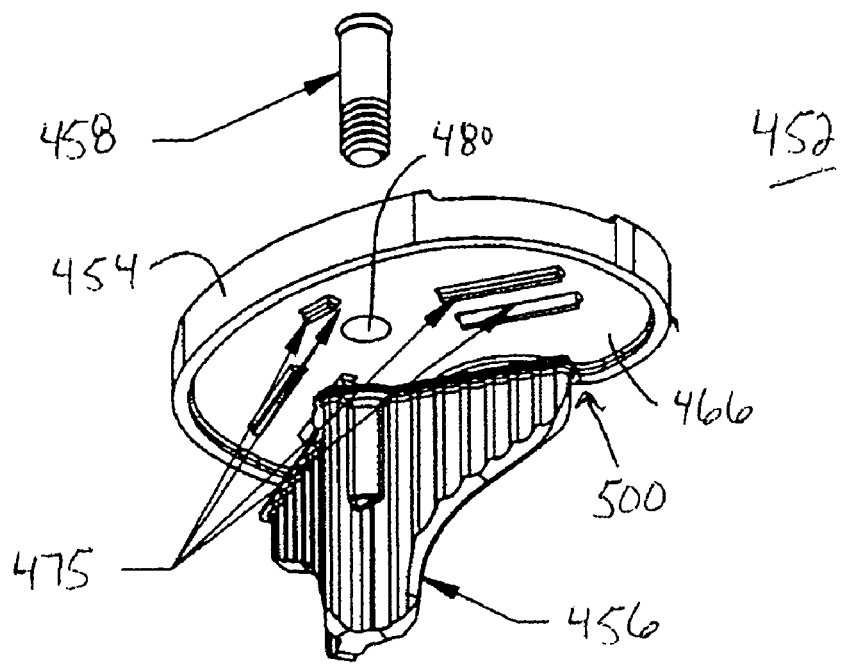
FIG. 39 shows a tibial implant, in accordance with yet further preferred embodiments of the present invention.

FIG. 39 shows a tibial implant 452 in accordance with another preferred embodiment of the present invention. The tibial implant includes a tibial baseplate 454 that is assembled with a keel 456. The bottom surface 466 of the tibial baseplate 454 includes one or more alignment guides 475 that project from the bottom surface 466 thereof. As will be described in more detail below, the alignment guides 475 have sloped surfaces that mirror sloping surfaces found at the proximal end of the keel 456. The meshing of the sloping surfaces of the alignment guide with the sloping surfaces at the proximal end of the keel provides for more secure locking between the keel and the baseplate.

Although not limited by any particular theory of operation, it is believed that the engagement of the sloping edges of the guide elements with the sloping edges at the proximal end of the keel prevents the baseplate from moving "horizontally" (i.e. in a direction parallel to the top surface of the tibial baseplate) relative to the keel after the locking element has been tightened.

Although not shown in FIG. 39 for purposes of clarity, the tibial baseplate 454 also preferably includes a barrier wall 484 that surrounds the opening 480 in the baseplate and the alignment guides 475 projecting from the bottom surface 466 of the baseplate 454. The barrier wall 484 has been removed from the remaining drawing figures showing this embodiment so that the alignment guides can be seen more clearly.

Figure 40A:
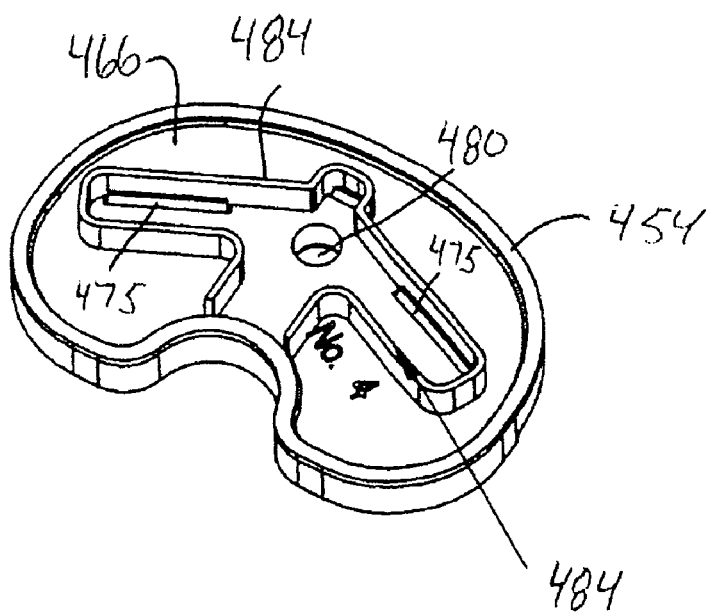
FIGS. 40A-40E show a tibial baseplate for the implant shown in FIG. 39.
Figure 40B:
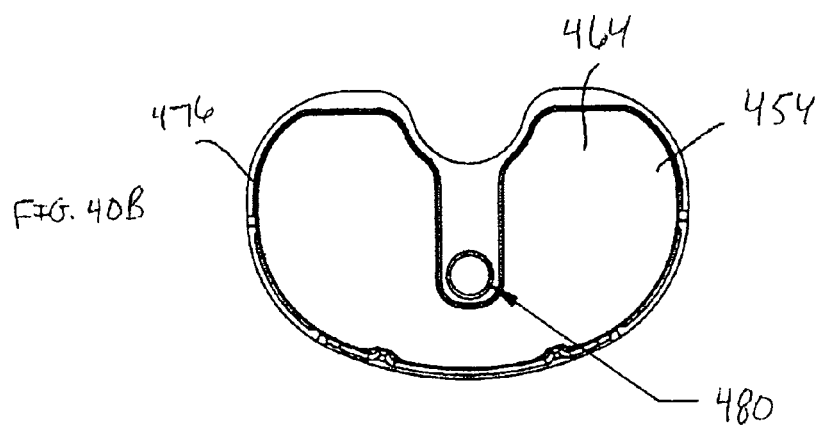
Figure 40C:
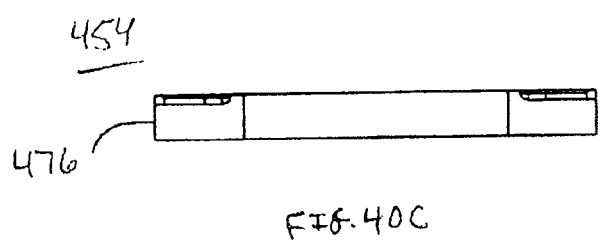

Referring to FIG. 40B, the tibial baseplate 454 includes upper surface 464 adapted to receive a bearing insert (not shown) and an opening 480 extending from the upper surface 464 to a bottom surface 466 (FIG. 39) of the baseplate. Referring to FIGS. 40B and 40C, the tibial baseplate 454 includes a rim 476 that surrounds an outer perimeter of the baseplate.

Figure 40D:
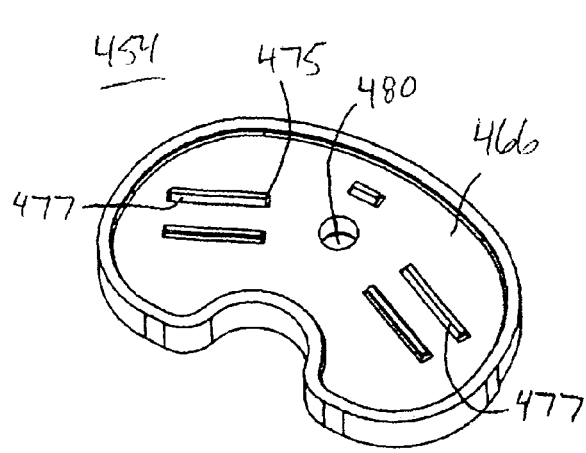
Figure 40E:
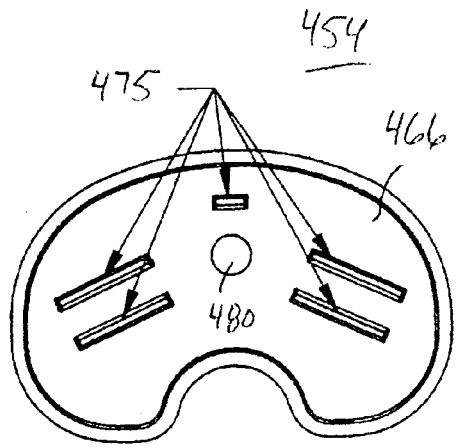
Figure 41A:
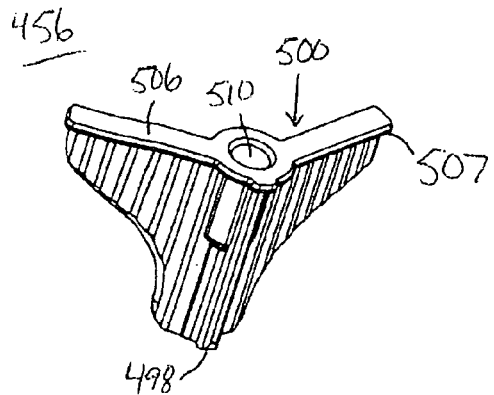
FIGS. 41A-41E show a keel for the tibial implant shown in FIG. 39.
Figure 41B:
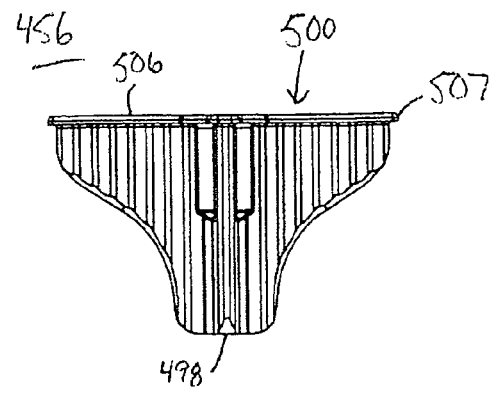
Figure 41C:
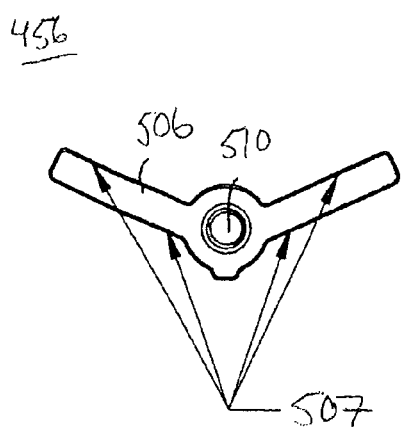
Figure 41D:
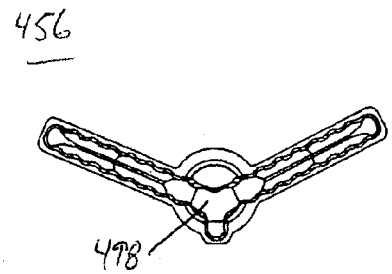
Figure 41E:
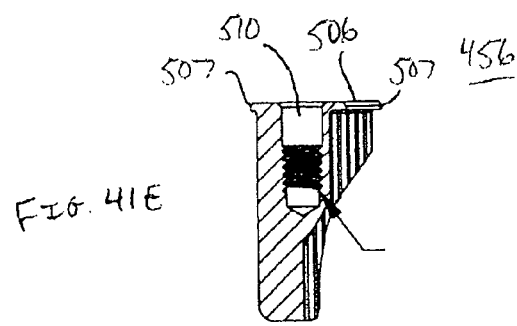
Figure 44:
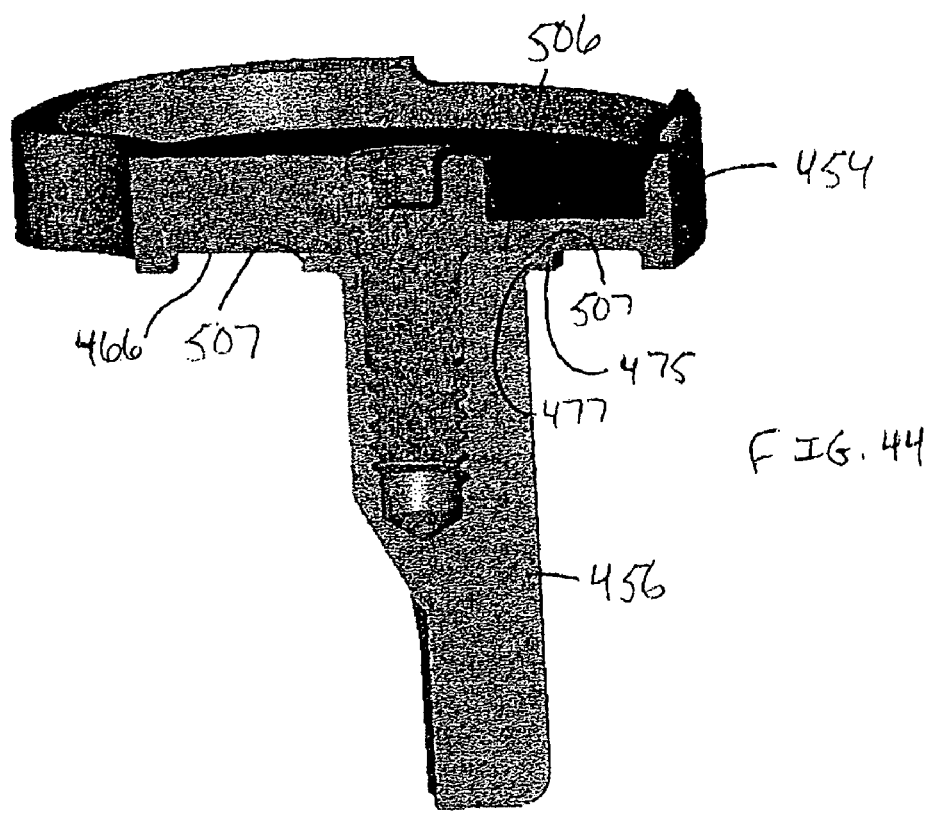
FIG. 44 shows another cross-sectional view of the tibial implant shown in FIG. 43.
Figure 45:
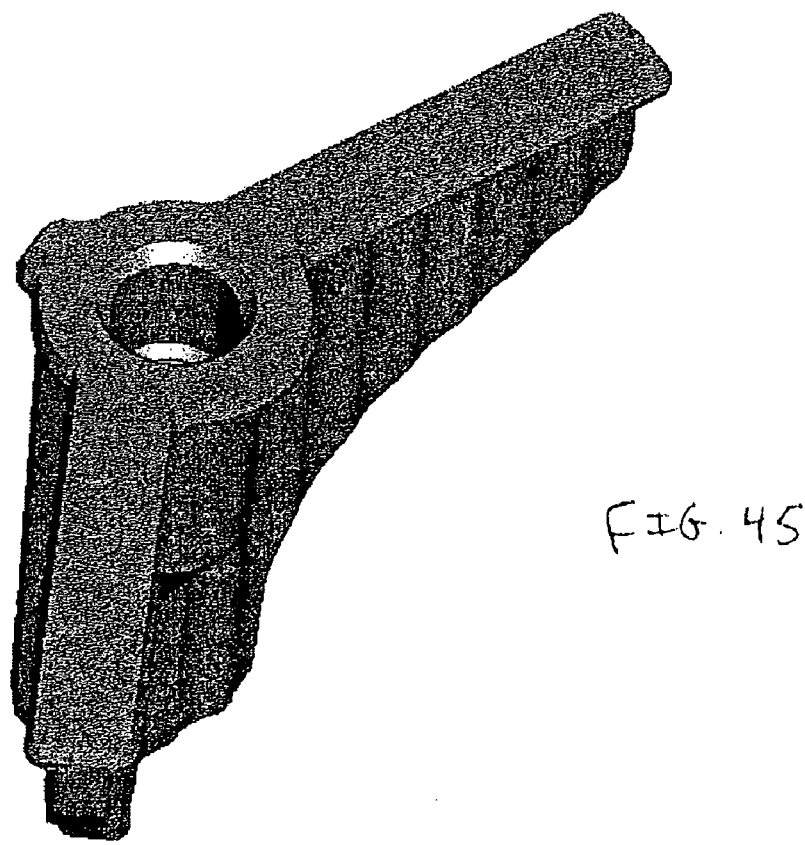
FIG. 45 shows a perspective view of the keel shown in FIG. 41A.
Figure 46:
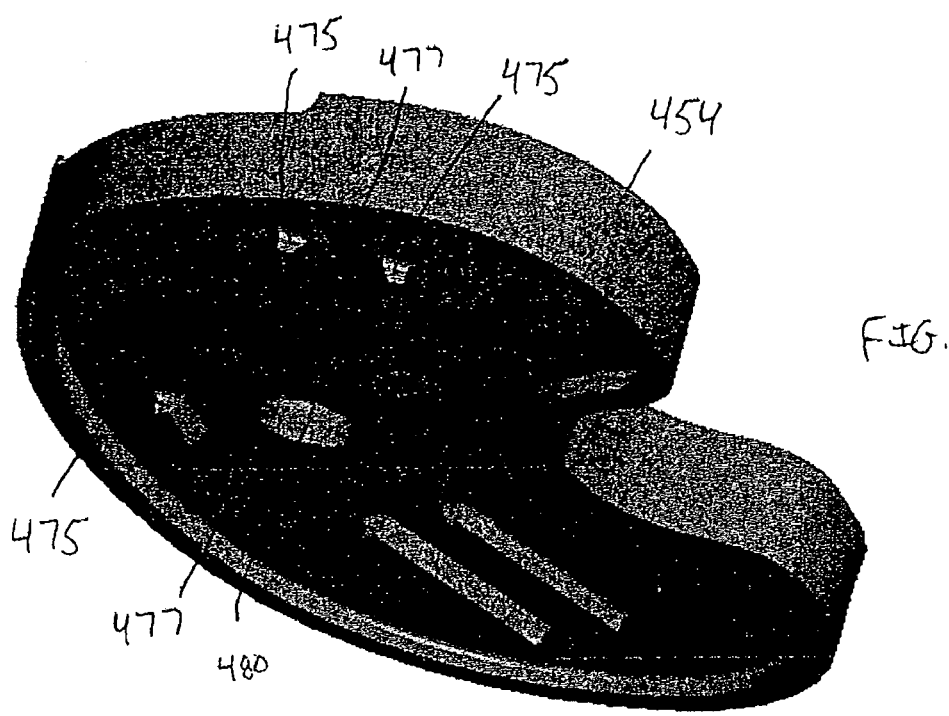
FIG. 46 shows a perspective view of the tibial baseplate shown in FIG. 40D.
Figure 47:
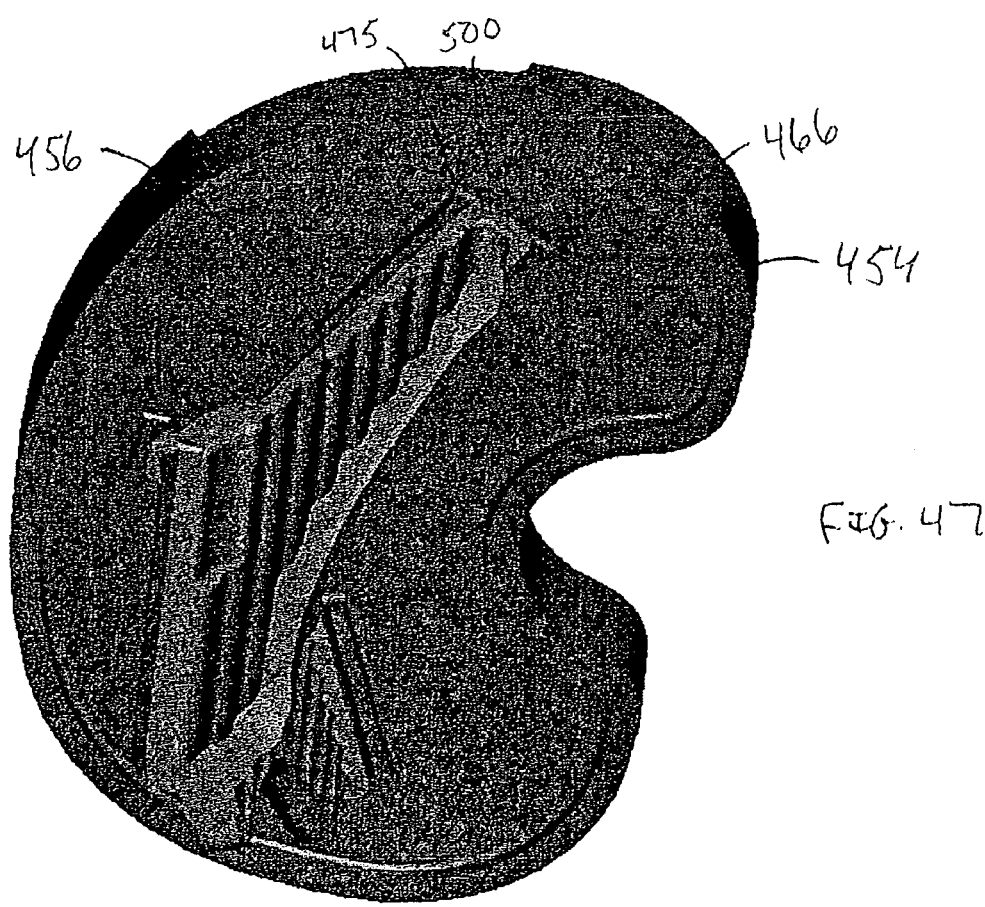
FIG. 47 shows a bottom perspective view of the tibial implant shown in FIG. 42C.

Referring to FIGS. 40D and 40E, the alignment guides 475 have sloped inner surfaces 477. As will be described in more detail below, the sloped surfaces 477 mesh with sloped peripheral surfaces at the proximal end of the keel for enhancing a locking force created between the proximal end of the keel and the bottom of the tibial baseplate.

FIGS. 41A-41E show a keel 456 that may be assembled with the bottom of a tibial baseplate. The keel 456 includes a distal end 498 and a proximal end 500. The proximal end has a bearing surface 506 that is adapted to be abutted against the bottom surface 466 of the tibial baseplate 454 (FIGS. 40D, 40E). The perimeter of the bearing surface 506 has a sloping edge 507 that mirrors the sloping edges of the alignment guides 477.

Referring to FIGS. 39, 42A-42C and 46-47, during assembly of the keel 456 with the tibial baseplate 454, the proximal end 500 the keel 456 is aligned with the guide elements 475 at the bottom surface 466 of the tibial baseplate 454. In addition, the opening 480 in the baseplate is aligned with the female opening 510 in the keel. The sloping edges 507 at the periphery of the bearing surface 506 are abutted against the sloping edges 477 of the guide elements 475. The locking element 458 is then passed through opening 480 in the baseplate and into the female opening 510 in the keel, and threaded into the threads of the female opening.

Referring to FIGS. 43-44 and 49-50, the bearing surface 506 at the proximal end of the keel engages the bottom surface 466 of the tibial baseplate 454. The locking element 458 holds the tibial baseplate 454 and the keel 456 together. In addition, the guide elements 475 engage the sloping surfaces at the outer edge of the proximal end of the keel 456 for further enhancing locking forces.

FIGS. 49 and 50 show the sloping surfaces 507 at the periphery of the bearing surface 506 engaging the sloping surfaces 477 of the guide elements 475 projecting from the bottom surface 466 of the tibial baseplate 454 for preventing horizontal movement of the tibial baseplate 454 relative to the keel 456.

While there has been described and illustrated embodiments of a tibial implant, it will be apparent to those skilled in the art that variations and modifications are possible without deviating from the broad spirit and principle of the present invention. The present invention shall, therefore, not be limited solely to the specific embodiments disclosed herein.

The invention claimed is:

1. A modular tibial implant comprising:
   a tibial baseplate having a top surface and a bottom surface and first and second through openings extending between the top and bottom surfaces;
   a bone engaging stem element mountable on the baseplate and having a distal end, a proximal end, and a longitudinal axis extending between the distal and proximal ends, the proximal end having a post extending proximally into the second through opening;
   a fastener engageable with said tibial baseplate and said bone engaging element for securing said tibial baseplate and said bone engaging stem element together, the fastener extending through the first through opening in the baseplate; and
   a cam element separate from said fastener and being engageable with a wall surrounding said second through opening in said tibial baseplate and the cam element having a bore for receiving said post on said bone engaging stem element for moving said baseplate relative to said bone engaging stem element along an axis that traverses the longitudinal axis of said bone engaging stem element.

2. The implant as claimed in claim 1, further comprising:
   the proximal end of said bone engaging stem element having a threaded opening aligned with the first through opening of said tibial baseplate, and the post at least partially inserted into the second through opening of said tibial baseplate;
   said fastener being a threaded fastener inserted into the aligned first through opening and threaded opening, wherein said threaded fastener is rotatable for securing said bone engaging stem element and said tibial baseplate together; and
   said cam element being inserted into the second through opening of said tibial baseplate for engaging the post, wherein said cam element is rotatably adjustable for moving said baseplate relative to said bone engaging stem element.

3. The implant as claimed in claim 1, wherein said cam element bore has an asymmetrical surface that engages the post located at the proximal end of said bone engaging stem element.

4. The implant as claimed in claim 1, wherein said post has a cross-section that is elongated along an axis.

5. The implant as claimed in claim 1, wherein said tibial baseplate has a periphery and a pin opening extending between the periphery and the second through opening of said tibial baseplate.

6. The implant as claimed in claim 5, wherein the pin opening is in communication with the second through opening of said tibial baseplate.

7. The implant as claimed in claim 6, further comprising a pin insertable into the pin opening for engaging said cam element after said cam element is inserted into the first through opening of said tibial baseplate and on to the post.

8. The implant as claimed in claim 7, wherein said cam element has a groove formed in an outer surface thereof and the pin engages the groove for limiting movement of said cam element.

9. The implant as claimed in claim 7, wherein said cam element has a groove formed in an outer surface thereof and the pin engages the groove for limiting rotation of said cam element.

10. The implant as claimed in claim 1, wherein said cam element bore has an opening having an asymmetrical surface that engages an outer surface of the post at the proximal end of said bone engaging element for moving said tibial baseplate relative to said bone engaging stem element when said cam element is rotated in a direction perpendicular to the longitudinal axis.

11. The implant as claimed in claim 1, wherein said bone engaging element is a keel or a stem.

\* \* \* \* \*